United States Patent
Kim et al.

(10) Patent No.: US 12,365,949 B2
(45) Date of Patent: Jul. 22, 2025

(54) METHOD FOR DIAGNOSING OVARIAN CANCER THROUGH MICROBIAL METAGENOME ANALYSIS

(71) Applicant: SEOUL NATIONAL UNIVERSITY R&DB FOUNDATION, Seoul (KR)

(72) Inventors: Yoon-Keun Kim, Gyeonggi-do (KR); Taesung Park, Seoul (KR); Yong Sang Song, Seoul (KR); Se Ik Kim, Seoul (KR)

(73) Assignee: SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 443 days.

(21) Appl. No.: 16/629,360

(22) PCT Filed: Feb. 23, 2018

(86) PCT No.: PCT/KR2018/002280
§ 371 (c)(1),
(2) Date: Jan. 8, 2020

(87) PCT Pub. No.: WO2018/155960
PCT Pub. Date: Aug. 30, 2018

(65) Prior Publication Data
US 2020/0199655 A1    Jun. 25, 2020

(30) Foreign Application Priority Data

Feb. 24, 2017  (KR) .......................... 10-2017-0024998
Feb. 22, 2018  (KR) .......................... 10-2018-0021197

(51) Int. Cl.
| | | |
|---|---|---|
| *C12Q 1/68* | (2018.01) | |
| *C12Q 1/686* | (2018.01) | |
| *C12Q 1/6886* | (2018.01) | |
| *C12Q 1/689* | (2018.01) | |

(52) U.S. Cl.
CPC ............ *C12Q 1/689* (2013.01); *C12Q 1/686* (2013.01); *C12Q 1/6886* (2013.01); *C12Q 2531/113* (2013.01)

(58) Field of Classification Search
CPC ...... C21Q 1/689; C12Q 1/6886; C12Q 1/686; C12Q 2531/113
See application file for complete search history.

(56) References Cited

U.S. PATENT DOCUMENTS

| | | | |
|---|---|---|---|
| 2008/0269129 A1 | 10/2008 | Sato et al. | |
| 2013/0203061 A1* | 8/2013 | Kuslich | G01N 33/57484 |
| | | | 435/6.12 |
| 2017/0369930 A1* | 12/2017 | Jee | C12Q 1/689 |
| 2018/0195111 A1* | 7/2018 | Gosiewski | C12Q 1/6869 |
| 2020/0199655 A1* | 6/2020 | Kim | C12Q 1/6886 |
| 2021/0189464 A1* | 6/2021 | Kim | C12Q 1/689 |

FOREIGN PATENT DOCUMENTS

| | | | | |
|---|---|---|---|---|
| JP | 2005505303 A | 2/2005 | | |
| KR | 20110025603 A | 3/2011 | | |
| KR | 20160073157 A | 6/2016 | | |
| WO | WO-2009100029 A1 * | 8/2009 | ............ | A61K 48/00 |
| WO | WO-2011127219 A1 * | 10/2011 | ........... | C12Q 1/6886 |
| WO | WO-2017009693 A1 * | 1/2017 | ............ | C12Q 1/686 |
| WO | WO-2018155960 A1 * | 8/2018 | ............ | C12Q 1/686 |

OTHER PUBLICATIONS

Banerjee, S., Tian, T., Wei, Z., Shih, N., Feldman, M.D., Alwine, J.C., Coukos, G. and Robertson, E.S., 2017. The ovarian cancer oncobiome. Oncotarget, 8(22), p. 36225-36255. (Year: 2017).*
Bashiardes S, Tuganbaev T, Federici S, Elinav E. The microbiome in anti-cancer therapy. Semin Immunol. 2017;32:74-81 (Year: 2017).*

(Continued)

*Primary Examiner* — Stephanie K Mummert
*Assistant Examiner* — Olayinka A Oyeyemi
(74) *Attorney, Agent, or Firm* — Riverside Law LLP

(57) ABSTRACT

The present invention relates to a method of diagnosing ovarian cancer through microbial metagenomic analysis, and more particularly to a method of diagnosing ovarian cancer by analyzing an increase or decrease in content of specific bacteria or archaea-derived extracellular vesicles through metagenomic analysis using a subject-derived sample. Extracellular vesicles secreted from microorganisms existing in the environment are absorbed into the human body, and thus may directly affect the occurrence of cancer, and it is difficult to diagnose ovarian cancer early before symptoms thereof so that efficient treatment thereof is difficult. Thus, according to the present invention, a risk for ovarian cancer can be predicted through metagenomic analysis of bacteria-derived extracellular vesicles using a human body-derived sample, and thus the onset of ovarian cancer can be delayed or ovarian cancer can be predicted through appropriate management by early diagnosis and prediction of a risk group for ovarian cancer, and even after ovarian cancer occurs, early diagnosis for ovarian cancer can be implemented, thereby lowering the incidence of ovarian cancer and increasing therapeutic effects.

2 Claims, 11 Drawing Sheets

Specification includes a Sequence Listing.

(56) References Cited

OTHER PUBLICATIONS

Runz et al., 2007. Malignant ascites-derived exosomes of ovarian carcinoma patients contain CD24 and EpCAM. Gynecologic oncology, 107(3), pp. 563-571. (Year: 2007).*

Tang, M.K. and Wong, A.S., 2015. Exosomes: Emerging biomarkers and targets for ovarian cancer. Cancer letters, 367(1), pp. 26-33. (Year: 2015).*

Schmelz, E.M., Roberts, P.C. and Ponder, M.A., 2014. Abstract LB-155: Ovarian cancer-induced changes in the intestinal microbiota as potential biomarkers for early detection. (Year: 2014).*

Sanschagrin, S. and Yergeau, E., 2014. Next-generation sequencing of 16S ribosomal RNA gene amplicons. JoVE (Journal of Visualized Experiments), (90) e51709 pp. 1-6. (Year: 2014).*

Yoo et al., 2016. 16S rRNA gene-based metagenomic analysis reveals differences in bacteria-derived extracellular vesicles in the urine of pregnant and non-pregnant women. Experimental & molecular medicine, 48(2) e208 pp. 1-8. (Year: 2016).*

Zhao, Z., Yang, Y., Zeng, Y. and He, M., 2016. A microfluidic ExoSearch chip for multiplexed exosome detection towards blood-based ovarian cancer diagnosis. Lab on a Chip, 16(3), pp. 489-496. (Year: 2016).*

Idahl et al., 2011. Chlamydia trachomatis and Mycoplasma genitalium plasma antibodies in relation to epithelial ovarian tumors. Infectious diseases in obstetrics and gynecology, pp. 1-11. (Year: 2011).*

Baldwin, D.A., Feldman, M., Alwine, J.C. and Robertson, E.S., 2014. Metagenomic assay for identification of microbial pathogens in tumor tissues. MBio, 5(5), pp. e01714-14. (Year: 2014).*

Brewster, W.R., Ko, E.M. and Keku, T.O., 2016. An evaluation of the microbiota of the upper genital tract of women with benign changes and epithelial ovarian cancer. (Year: 2016).*

Shanmughapriya S, et al. Viral and bacterial aetiologies of epithelial ovarian cancer. Eur J Clin Microbiol Infect Dis. 2012;31:2311-2317. (Year: 2012).*

English Translation of KR-10-2018-009154A (filed Feb. 22, 2018, published Sep. 3, 2018) (Year: 2018).*

Banerjee et al., 2017. The ovarian cancer oncobiome. Oncotarget, 8(22), p. 36225-36245. (Year: 2017).*

* cited by examiner

METHOD FOR DIAGNOSING OVARIAN CANCER THROUGH MICROBIAL METAGENOME ANALYSIS

CROSS-REFERENCE TO RELATED APPLICATIONS

This application is the U.S. national phase application filed under 35 U.S.C. § 371 claiming benefit to International Patent Application No. PCT/KR2018/002280, filed on Feb. 23, 2018, which claims priority to Korean Patent Application No. 10-2017-0024998, filed Feb. 24, 2017, and Korean Patent Application No. 10-2018-0021197, filed Feb. 22, 2018, the disclosures of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0081-00US_Sequence_Listing_ST25.txt" in ASCII format. The text file containing the Sequence Listing of the present application was created on Nov. 15, 2021, and is 954 bytes in size.

TECHNICAL FIELD

The present invention relates to a method of diagnosing ovarian cancer through bacterial metagenomic analysis, and more particularly, to a method of diagnosing ovarian cancer by analyzing an increase or decrease in content of extracellular vesicles derived from specific bacteria and archaea by metagenomic analysis of microorganisms such as bacteria and archaea using a subject-derived sample.

BACKGROUND ART

Ovarian cancer is the second most common genital cancer. However, 70% of women are diagnosed at an advanced stage, so the treatment rate is only 20% to 30%. The causes of ovarian cancer are not yet been known exactly, like other cancers. For some factors, women who have family members with ovarian cancer have a high risk of ovarian cancer, but 95% of ovarian cancer patients have no family history. If women, who have a family history of breast cancer, endometrial cancer, or rectal cancer, develop breast cancer, they are 2 times more likely to develop ovarian cancer. Persistent ovulation and menstruation are known to increase the risk of ovarian cancer. In contrast, pregnancy tends to prevent the occurrence of ovarian cancer, and thus the risk of ovarian cancer decreases by about 10% in women with 1 childbirth and by 50% in women with 3 childbirths, compared to women who never give birth. Breastfeeding after birth also reduces the number of ovulations to reduce the occurrence of ovarian cancer. Due to environmental factors, ovarian cancer more commonly occurs in developed countries and urban women, and obesity and infectivity of various viral diseases are also known to be associated with the development of ovarian cancer.

For ovarian cancer diagnosis, vaginal ultrasound and tumor markers are mainly used, and as tumor indicators, CA125, CA19-9, AFP, CEA, SA, CA72.4, and the like are used. Among these, CA125 is widely used for screening, diagnosis, monitoring, and follow-ups. However, there are limitations such as low specificity and low sensitivity in stage 1 and stage 2 ovarian cancer.

Meanwhile, it is known that the number of microorganisms symbiotically living in the human body is 100 trillion which is 10 times the number of human cells, and the number of genes of microorganisms exceeds 100 times the number of human genes. A microbiota or microbiome is a microbial community that includes bacteria, archaea, and eukaryotes present in a given habitat. The intestinal microbiota is known to play a vital role in human's physiological phenomena and significantly affect human health and diseases through interactions with human cells. Bacteria coexisting in human bodies secrete nanometer-sized vesicles to exchange information about genes, proteins, and the like with other cells. The mucous membranes form a physical barrier membrane that does not allow particles with the size of 200 nm or more to pass therethrough, and thus bacteria symbiotically living in the mucous membranes are unable to pass therethrough, but bacteria-derived extracellular vesicles have a size of approximately 100 nm or less and thus relatively freely pass through the mucous membranes and are absorbed into the human body.

Metagenomics, also called environmental genomics, may be analytics for metagenomic data obtained from samples collected from the environment (Korean Patent Publication No. 2011-073049). Recently, the bacterial composition of human microbiota has been listed using a method based on 16s ribosomal RNA (16s rRNA) base sequences, and 16s rDNA base sequences, which are genes of 16s ribosomal RNA, are analyzed using a next generation sequencing (NGS) platform. However, in the onset of ovarian cancer, identification of causative factors of ovarian cancer through metagenomic analysis of microorganisms-derived vesicles isolated from a human-derived substance, such as blood or urine and the like, and a method of predicting ovarian cancer have never been reported.

DISCLOSURE

Technical Problem

The inventors isolated extracellular vesicles from subject-derived samples such as blood and urine, extracted genes from the vesicles, and conducted metagenomic analysis thereof to diagnose ovarian cancer. As a result, bacteria- and archaea-derived extracellular vesicles, which can serve as causative factors of ovarian cancer were identified, and based on this, the present invention was completed.

Therefore, the present invention was directed to providing a method of providing information to diagnose ovarian cancer through metagenomic analysis of bacteria- and archaea-derived extracellular vesicles, a method of diagnosing ovarian cancer, and a method of predicting the risk of the onset of ovarian cancer.

However, the technical goals of the present invention are not limited to the aforementioned goals, and other unmentioned technical goals will be clearly understood by those of ordinary skill in the art from the following description.

Technical Solution

To achieve the above-described object of the present invention, there is provided a method of providing information for ovarian cancer diagnosis, comprising the following processes:

(a) extracting DNAs from extracellular vesicles isolated from subject samples;
(b) performing polymerase chain reaction (PCR) on the extracted DNA using a pair of primers comprising SEQ ID NO: 1 and SEQ ID NO: 2; and
(c) comparing an increase or decrease in content of bacteria- and archaea-derived extracellular vesicles of the subject-derived sample with that of a normal individual-derived sample through sequencing of a product of the PCR.

The present invention also provides a method of diagnosing ovarian cancer, comprising the following processes:
(a) extracting DNAs from extracellular vesicles isolated from subject samples;
(b) performing polymerase chain reaction (PCR) on the extracted DNA using a pair of primers comprising SEQ ID NO: 1 and SEQ ID NO: 2; and
(c) comparing an increase or decrease in content of bacteria- and archaea-derived extracellular vesicles of the subject-derived sample with that of a normal individual-derived sample through sequencing of a product of the PCR.

The present invention also provides a method of predicting a risk for ovarian cancer, comprising the following processes:
(a) extracting DNAs from extracellular vesicles isolated from subject samples;
(b) performing polymerase chain reaction (PCR) on the extracted DNA using a pair of primers comprising SEQ ID NO: 1 and SEQ ID NO: 2; and
(c) comparing an increase or decrease in content of bacteria- and archaea-derived extracellular vesicles of the subject-derived sample with that of a normal individual-derived sample through sequencing of a product of the PCR.

In one embodiment of the present invention, the subject samples may be blood or urine.

In another embodiment of the present invention, process (c) may comprise comparing an increase or decrease in content of extracellular vesicles derived from one or more bacteria selected from the group consisting of the class Erysipelotrichi, the class Alphaproteobacteria, the class Coriobacteriia, the class Flavobacteriia, the class Oscillatoriophycideae, the class Deltaproteobacteria, and the class ML635J-21 that are isolated from the subject blood sample.

In another embodiment of the present invention, process (c) may comprise comparing an increase or decrease in content of extracellular vesicles derived from one or more bacteria selected from the group consisting of the order Erysipelotrichales, the order Rhizobiales, the order Caulobacterales, the order Pseudomonadales, the order Coriobacteriales, the order Flavobacteriales, the order YS2, the order Chroococcales, the order CW040, the order Desulfovibrionales, and the order Methylophilales that are isolated from the subject blood sample.

In another embodiment of the present invention, process (c) may comprise comparing an increase or decrease in content of extracellular vesicles derived from one or more bacteria selected from the group consisting of the family Rhizobiaceae, the family Bradyrhizobiaceae, the family Peptostreptococcaceae, the family Oxalobacteraceae, the family Erysipelotrichaceae, the family Pseudomonadaceae, the family Caulobacteraceae, the family Methylobacteriaceae, the family Paraprevotellaceae, the family Fusobacteriaceae, the family Planococcaceae, the family Burkholderiaceae, the family Aerococcaceae, the family Lactobacillaceae, the family Coriobacteriaceae, the family Weekselaceae, the family Xenococcaceae, the family F16, the family Desulfovibrionaceae, the family Comamonadaceae, the family S24-7, and the family Methylophilaceae that are isolated from the subject blood sample.

In another embodiment of the present invention, process (c) may comprise comparing an increase or decrease in content of extracellular vesicles derived from one or more bacteria selected from the group consisting of the genus *Morganella*, the genus *Hydrogenophilus*, the genus *Cupriavidus*, the genus *Eubacterium*, the genus *Catenibacterium*, the genus *Micrococcus*, the genus *Coprococcus*, the genus *Pseudomonas*, the genus *Paraprevotella*, the genus *Sphingomonas*, the genus *Faecalibacterium*, the genus *Blautia*, the genus *Serratia*, the genus *Citrobacter*, and the genus *Collinsella* that are isolated from the subject blood sample.

In another embodiment of the present invention, process (c) may comprise comparing an increase or decrease in content of extracellular vesicles derived from one or more bacteria selected from the group consisting of the phylum Tenericutes, the phylum Deferribacteres, the phylum Fusobacteria, the phylum Armatimonadetes, the phylum SR1, the phylum Gemmatimonadetes, and the phylum TM6 that are isolated from the subject urine sample.

In another embodiment of the present invention, process (c) may comprise comparing an increase or decrease in content of extracellular vesicles derived from one or more bacteria selected from the group consisting of the class Mollicutes, the class Deferribacteres, the class Fusobacteriia, the class Fimbriimonadia, the class Erysipelotrichi, the class Chloroplast, the class Gammaproteobacteria, the class Betaproteobacteria, the class Bacilli, the class Acidimicrobiia, the class Deltaproteobacteria, the class Oscillatoriophycideae, the class 4C0d-2, the class Gemmatimonadetes, the class Flavobacteriia, the class ML635J-21, and the class SJA-4 that are isolated from the subject urine sample.

In another embodiment of the present invention, process (c) may comprise comparing an increase or decrease in content of extracellular vesicles derived from one or more bacteria selected from the group consisting of the order Desulfuromonadales, the order Desulfobacterales, the order Gallionellales, the order Cardiobacteriales, the order Stramenopiles, the order Marinicellales, the order Halanaerobiales, the order RF39, the order Deferribacterales, the order Pirellulales, the order Fusobacteriales, the order Fimbriimonadales, the order Erysipelotrichales, the order Pseudomonadales, the order Streptophyta, the order Turicibacterales, the order Burkholderiales, the order Sphingomonadales, the order Myxococcales, the order Thermales, the order YS2, the order Bacillales, the order Acidimicrobiales, the order Oceanospirillales, the order Legionellales, the order iii1-15, the order Chroococcales, the order CW040, the order EW055, the order Gemmatimonadales, the order Flavobacteriales, the order Rhodocyclales, the order Desulfovibrionales, the order MLE1-12, the order Methylophilales, and the order Ellin6067 that are isolated from the subject urine sample.

In another embodiment of the present invention, process (c) may comprise comparing an increase or decrease in content of extracellular vesicles derived from one or more bacteria selected from the group consisting of the family Cardiobacteriaceae, the family Acidobacteriaceae, the family Oxalobacteraceae, the family Prevotellaceae, the family Leptotrichiaceae, the family Chris tensenellaceae, the family Barnesiellaceae, the family Fimbriimonadaceae, the family Erysipelotrichaceae, the family Mogibacteriaceae, the family Pseudomonadaceae, the family Fusobacteriaceae, the family Pseudonocardiaceae, the family Leuconostocaceae, the family Moraxellaceae, the family Methylobacteriaceae, the family Paraprevotellaceae, the family Sphingomonadaceae, the family Nocardioidaceae, the family Lactobacillaceae, the family Burkholderiaceae, the family Aerococcaceae, the family Nocardiopsaceae, the family Rhodocyclaceae, the family S24-7, the family Eubacteriaceae, the family Des ulfovibrionaceae, the family Comamonadaceae, the family Methylophilaceae, and the family Coxiellaceae that are isolated from the subject urine sample.

In another embodiment of the present invention, process (c) may comprise comparing an increase or decrease in content of extracellular vesicles derived from one or more bacteria selected from the group consisting of the genus *Morganella*, the genus *Rhizobium*, the genus *Exiguobacterium*, the genus *Cupriavidus*, the genus *Ralstonia*, the genus *Cellulomonas*, the genus *Sporosarcina*, the genus *Proteus*, the genus *Leptotrichia*, the genus SMB53, the genus *Prevotella*, the genus *Oribacterium*, the genus *Pediococcus*, the genus *Paraprevotella*, the genus *Methylobacterium*, the genus *Mucispirillum*, the genus *Catenibacterium*, the genus *Parabacteroides*, the genus *Collinsella*, the genus *Anaerostipes*, the genus *Pseudomonas*, the genus *Butyricimonas*, the genus *Fusobacterium*, the genus *Weissella*, the genus *Eubacterium*, the genus *Dialister*, the genus *Actinomyces*, the genus *Odoribacter*, the genus *Sphingomonas*, the genus *Bacteroides*, the genus *Turicibacter*, the genus *Enterococcus*, the genus *Dorea*, the genus *Lactobacillus*, the genus *Erwinia*, the genus *Staphylococcus*, the genus *Citrobacter*, the genus *Halomonas*, the genus *Sphingobium*, the genus *Gordonia*, the genus *Adlercreutzia*, the genus *Brevibacillus*, the genus *Aerococcus*, the genus *Salinicoccus*, the genus *Jeotgalicoccus*, the genus *Desulfovibrio*, the genus *Burkholderia*, the genus *Novosphingobium*, the genus *Comamonas*, the genus *Cloacibacterium*, the genus *Dechloromonas*, the genus *Thermomonas*, the genus *Diaphorobacter*, the genus *Pedomicrobium*, the genus KD1-23, the genus *Zoogloea*, the genus *Methylophaga*, and the genus *Haererehalobacter* that are isolated from the subject urine sample.

In still another embodiment of the present invention, the blood may be whole blood, serum, plasma, or blood mononuclear cells.

Advantageous Effects

Extracellular vesicles secreted from bacteria existing in the environment are absorbed into the human body, and thus may directly affect the occurrence of cancer, and it is difficult to diagnose ovarian cancer early before symptoms thereof so that efficient treatment thereof is difficult. Thus, according to the present invention, a risk for ovarian cancer can be predicted through metagenomic analysis of bacteria-derived extracellular vesicles using a human body-derived sample, and thus the onset of ovarian cancer can be delayed or ovarian cancer can be predicted through appropriate management by early diagnosis and prediction of a risk group for ovarian cancer, and even after ovarian cancer occurs, early diagnosis for ovarian cancer can be implemented, thereby lowering the incidence of ovarian cancer and increasing therapeutic effects. In addition, the metagenomic analysis enables patients diagnosed with ovarian cancer to avoid exposure to causative factors predicted thereby, whereby the progression of cancer is ameliorated, or the recurrence of ovarian cancer can be prevented.

BEST MODE

Figure 1A:
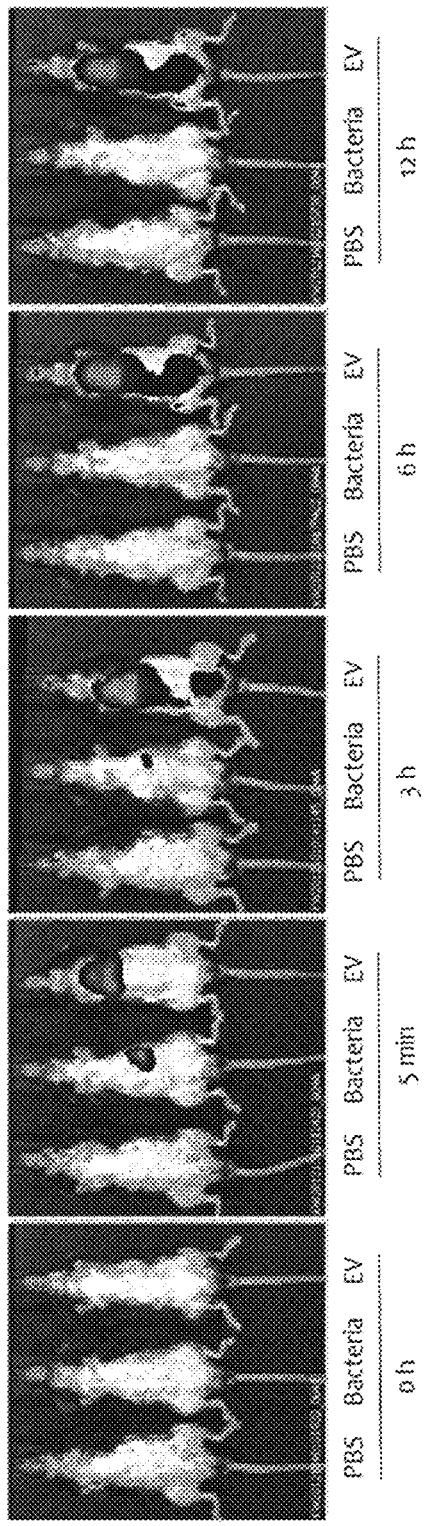
FIG. 1A illustrates images showing the distribution pattern of bacteria and extracellular vesicles over time after intestinal bacteria and bacteria-derived extracellular vesicles (EVs) were orally administered to mice.

The present invention relates to a method of diagnosing ovarian cancer through microorganisms metagenomic analysis. The inventors of the present invention extracted genes from extracellular vesicles using a subject-derived sample, performed metagenomic analysis thereon, and identified bacteria-derived extracellular vesicles capable of acting as a causative factor of ovarian cancer.

Therefore, the present invention provides a method of providing information for diagnosing ovarian cancer, the method comprising:

(a) extracting DNAs from extracellular vesicles isolated from subject samples;
(b) performing polymerase chain reaction (PCR) on the extracted DNA using a pair of primers comprising SEQ ID NO: 1 and SEQ ID NO: 2; and
(c) comparing an increase or decrease in content of bacteria- and archaea-derived extracellular vesicles of the subject-derived sample with that of a normal individual-derived sample through sequencing of a product of the PCR.

The term "ovarian cancer diagnosis" as used herein refers to determining whether a patient has a risk for ovarian cancer, whether the risk for ovarian cancer is relatively high, or whether ovarian cancer has already occurred. The method of the present invention may be used to delay the onset of ovarian cancer through special and appropriate care for a specific patient, which is a patient having a high risk for ovarian cancer or prevent the onset of ovarian cancer. In addition, the method may be clinically used to determine treatment by selecting the most appropriate treatment method through early diagnosis of ovarian cancer.

The term "metagenome" as used herein refers to the total of genomes including all viruses, bacteria, fungi, and the like in isolated regions such as soil, the intestines of animals, and the like, and is mainly used as a concept of genomes that explains identification of many microorganisms at once using a sequencer to analyze non-cultured microorganisms. In particular, a metagenome does not refer to a genome of one species, but refers to a mixture of genomes, including genomes of all species of an environmental unit. This term originates from the view that, when defining one species in a process in which biology is advanced into omics, various species as well as existing one species functionally interact with each other to form a complete species. Technically, it is the subject of techniques that analyzes all DNAs and RNAs regardless of species using rapid sequencing to identify all species in one environment and verify interactions and metabolism. In the present invention, bacterial metagenomic analysis is performed using bacteria-derived extracellular vesicles isolated from, for example, blood and urine.

The term "bacteria-derived vesicles" used herein is the generic term for extracellular vesicles secreted from archaea as well as bacteria, but the present invention is not limited thereto.

In the present invention, the subject samples may be blood or urine, and the blood is preferably whole blood, serum, plasma or blood monocytes, but the present invention is not limited thereto.

In an embodiment of the present invention, metagenomic analysis is performed on the bacteria- and archaea-derived extracellular vesicles, and bacteria-derived extracellular vesicles capable of acting as a cause of the onset of ovarian cancer were actually identified by analysis at phylum, class, order, family, and genus levels.

More particularly, in one embodiment of the present invention, as a result of performing bacterial metagenomic analysis on extracellular vesicles present in subject-derived blood samples at a class level, the content of extracellular vesicles derived from bacteria belonging to the class Erysipelotrichi, the class Alphaproteobacteria, the class Coriobacteriia, the class Flavobacteriia, the class Oscillatoriophycideae, the class Deltaproteobacteria, and the class ML635J-21 was significantly different between ovarian cancer patients and normal individuals (see Example 4).

More particularly, in one embodiment of the present invention, as a result of performing bacterial metagenomic analysis on extracellular vesicles present in subject-derived blood samples at an order level, the content of extracellular vesicles derived from bacteria belonging to the order Erysipelotrichales, the order Rhizobiales, the order Caulobacterales, the order Pseudomonadales, the order Coriobacteriales, the order Flavobacteriales, the order YS2, the order Chroococcales, the order CW040, the order Desulfovibrionales, and the order Methylophilales was significantly different between ovarian cancer patients and normal individuals (see Example 4).

More particularly, in one embodiment of the present invention, as a result of performing bacterial metagenomic analysis on extracellular vesicles present in subject-derived blood samples at a family level, the content of extracellular vesicles derived from bacteria belonging to the family Rhizobiaceae, the family Bradyrhizobiaceae, the family Peptostreptococcaceae, the family Oxalobacteraceae, the family Erysipelotrichaceae, the family Pseudomonadaceae, the family Caulobacteraceae, the family Methylobacteriaceae, the family Paraprevotellaceae, the family Fusobacteriaceae, the family Planococcaceae, the family Burkholderiaceae, the family Aerococcaceae, the family Lactobacillaceae, the family Coriobacteriaceae, the family Weeksellaceae, the family Xenococcaceae, the family F16, the family Desulfovibrionaceae, the family Comamonadaceae, the family S24-7, and the family Methylophilaceae was significantly different between ovarian cancer patients and normal individuals (see Example 4).

More particularly, in one embodiment of the present invention, as a result of performing bacterial metagenomic analysis on extracellular vesicles present in subject-derived blood samples at a genus level, the content of extracellular vesicles derived from bacteria belonging to the genus *Morganella*, the genus *Hydrogenophilus*, the genus *Cupriavidus*, the genus *Eubacterium*, the genus *Catenibacterium*, the genus *Micrococcus*, the genus *Coprococcus*, the genus *Pseudomonas*, the genus *Paraprevotella*, the genus *Sphingomonas*, the genus *Faecalibacterium*, the genus *Blautia*, the genus *Serratia*, the genus *Citrobacter*, and the genus *Collinsella* was significantly different between ovarian cancer patients and normal individuals (see Example 4).

More particularly, in one embodiment of the present invention, as a result of performing bacterial metagenomic analysis on extracellular vesicles present in subject-derived urine samples at a phylum level, the content of extracellular vesicles derived from bacteria belonging to the phylum Tenericutes, the phylum Deferribacteres, the phylum Fusobacteria, the phylum Armatimonadetes, the phylum SR1, the phylum Gemmatimonadetes, and the phylum TM6 was significantly different between ovarian cancer patients and normal individuals (see Example 5).

More particularly, in one embodiment of the present invention, as a result of performing bacterial metagenomic analysis on extracellular vesicles present in subject-derived urine samples at a class level, the content of extracellular vesicles derived from bacteria belonging to the class Mollicutes, the class Deferribacteres, the class Fusobacteriia, the class Fimbriimonadia, the class Erysipelotrichi, the class Chloroplast, the class Gammaproteobacteria, the class Betaproteobacteria, the class Bacilli, the class Acidimicrobiia, the class Deltaproteobacteria, the class Oscillatoriophycideae, the class 4C0d-2, the class Gemmatimonadetes, the class Flavobacteriia, the class ML635J-21, and the class SJA-4 was significantly different between ovarian cancer patients and normal individuals (see Example 5).

More particularly, in one embodiment of the present invention, as a result of performing bacterial metagenomic analysis on extracellular vesicles present in subject-derived urine samples at an order level, the content of extracellular vesicles derived from bacteria belonging to the order Desulfuromonadales, the order Desulfobacterales, the order Gallionellales, the order Cardiobacteriales, the order Stramenopiles, the order Marinicellales, the order Halanaerobiales, the order RF39, the order Deferribacterales, the order Pirellulales, the order Fusobacteriales, the order Fimbriimonadales, the order Erysipelotrichales, the order Pseudomonadales, the order Streptophyta, the order Turicibacterales, the order Burkholderiales, the order Sphingomonadales, the order Myxococcales, the order Thermales, the order YS2, the order Bacillales, the order Acidimicrobiales, the order Oceanospirillales, the order Legionellales, the order iii1-15, the order Chroococcales, the order CW040, the order EW055, the order Gemmatimonadales, the order Flavobacteriales, the order Rhodocyclales, the order Desulfovibrionales, the order MLE1-12, the order Methylophilales, and the order Ellin6067 was significantly different between ovarian cancer patients and normal individuals (see Example 5).

More particularly, in one embodiment of the present invention, as a result of performing bacterial metagenomic analysis on extracellular vesicles present in subject-derived urine samples at a family level, the content of extracellular vesicles derived from bacteria belonging to the family Cardiobacteriaceae, the family Acidobacteriaceae, the family Oxalobacteraceae, the family Prevotellaceae, the family Leptotrichiaceae, the family Christensenellaceae, the family Barnesiellaceae, the family Fimbriimonadaceae, the family Erysipelotrichaceae, the family Mogibacteriaceae, the family Pseudomonadaceae, the family Fusobacteriaceae, the family Pseudonocardiaceae, the family Leuconostocaceae, the family Moraxellaceae, the family Methylobacteriaceae, the family Paraprevotellaceae, the family Sphingomonadaceae, the family Nocardioidaceae, the family Lactobacillaceae, the family Burkholderiaceae, the family Aerococcaceae, the family Nocardiopsaceae, the family Rhodocyclaceae, the family S24-7, the family Eubacteriaceae, the family Desulfovibrionaceae, the family Comamonadaceae, the family Methylophilaceae, and the family Coxiellaceae was significantly different between ovarian cancer patients and normal individuals (see Example 5).

More particularly, in one embodiment of the present invention, as a result of performing bacterial metagenomic analysis on extracellular vesicles present in subject-derived urine samples at a genus level, the content of extracellular vesicles derived from bacteria belonging to the genus Morganella, the genus Rhizobium, the genus Exiguobacterium, the genus Cupriavidus, the genus Ralstonia, the genus Cellulomonas, the genus Sporosarcina, the genus Proteus, the genus Leptotrichia, the genus SMB53, the genus Prevotella, the genus Oribacterium, the genus Pediococcus, the genus Paraprevotella, the genus Methylobacterium, the genus Mucispirillum, the genus Catenibacterium, the genus Parabacteroides, the genus Collinsella, the genus Anaerostipes, the genus Pseudomonas, the genus Butyricimonas, the genus Fusobacterium, the genus Weissella, the genus Eubacterium, the genus Dialister, the genus Actinomyces, the genus Odoribacter, the genus Sphingomonas, the genus Bacteroides, the genus Turicibacter, the genus Enterococcus, the genus Dorea, the genus Lactobacillus, the genus Erwinia, the genus Staphylococcus, the genus Citrobacter, the genus Halomonas, the genus Sphingobium, the genus Gordonia, the genus Adlercreutzia, the genus Brevibacillus, the genus Aerococcus, the genus Salinicoccus, the genus Jeotgalicoccus, the genus Desulfovibrio, the genus Burkholderia, the genus Novosphingobium, the genus Comamonas, the genus Cloacibacterium, the genus Dechloromonas, the genus Thermomonas, the genus Diaphorobacter, the genus Pedomicrobium, the genus KD1-23, the genus Zoogloea, the genus Methylophaga, and the genus Haererehalobacter was significantly different between ovarian cancer patients and normal individuals (see Example 5).

According to the result of the exemplary embodiment of the present invention described above, bacteria-derived extracellular vesicles, which are isolated from blood and urine, were compared with those of a normal individual sample through metagenomic analysis, thereby identifying bacteria-derived vesicles, which are significantly changed in content, in an ovarian cancer patient, and an increase or decrease in content of bacteria-derived vesicles at the above-mentioned level was analyzed through metagenomic analysis, confirming that ovarian cancer can be diagnosed.

Hereinafter, the present invention will be described with reference to exemplary examples to aid in understanding of the present invention. However, these examples are provided only for illustrative purposes and are not intended to limit the scope of the present invention.

Mode of the Invention

EXAMPLES

Example 1 Analysis of In Vivo Absorption, Distribution, and Excretion Patterns of Intestinal Bacteria and Bacteria-Derived Extracellular Vesicles To evaluate whether intestinal bacteria and bacteria-derived extracellular vesicles are systematically absorbed through the gastrointestinal tract, an experiment was conducted using the following method. More particularly, 50 µg of each of intestinal bacteria and the bacteria-derived extracellular vesicles (EVs), labeled with fluorescence, were orally administered to the gastrointestinal tracts of mice, and fluorescence was measured at 0 h, and after 5 min, 3 h, 6 h, and 12 h. As a result of observing the entire images of mice, as illustrated in FIG. 1A, the bacteria were not systematically absorbed when administered, while the bacteria-derived EVs were systematically absorbed at 5 min after administration, and, at 3 h after administration, fluorescence was strongly observed in the bladder, from which it was confirmed that the EVs were excreted via the urinary system, and were present in the bodies up to 12 h after administration.

Figure 1B:
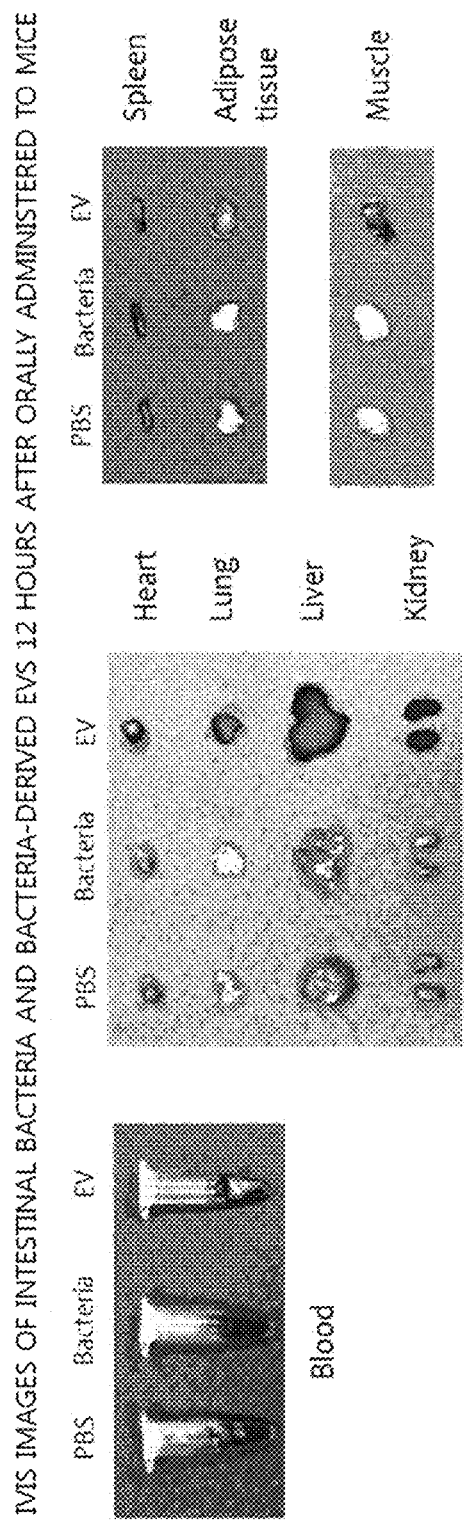
FIG. 1B illustrates images showing the distribution pattern of bacteria and EVs after being orally administered to mice and, at 12 hours, blood and various organs were extracted.

After intestinal bacteria and intestinal bacteria-derived extracellular vesicles were systematically absorbed, to evaluate a pattern of invasion of intestinal bacteria and the bacteria-derived EVs into various organs in the human body after being systematically absorbed, 50 µg of each of the bacteria and bacteria-derived EVs, labeled with fluorescence, were administered using the same method as that used above, and then, at 12 h after administration, blood, the heart, the lungs, the liver, the kidneys, the spleen, adipose tissue, and muscle were extracted from each mouse. As a result of observing fluorescence in the extracted tissues, as illustrated in FIG. 1B, it was confirmed that the intestinal bacteria were not absorbed into each organ, while the bacteria-derived EVs were distributed in the blood, heart, lungs, liver, kidneys, spleen, adipose tissue, and muscle.

Example 2 Vesicle Isolation and DNA Extraction from Blood and Urine

To isolate extracellular vesicles and extract DNA, from blood and urine, first, blood or urine was added to a 10 ml tube and centrifuged at 3,500×g and 4° C. for 10 min to precipitate a suspension, and only a supernatant was collected, which was then placed in a new 10 ml tube. The collected supernatant was filtered using a 0.22 μm filter to remove bacteria and impurities, and then placed in centrifugal filters (50 kD) and centrifuged at 1500×g and 4□ for 15 min to discard materials with a smaller size than 50 kD, and then concentrated to 10 ml. Once again, bacteria and impurities were removed therefrom using a 0.22 μm filter, and then the resulting concentrate was subjected to ultra-high speed centrifugation at 150,000×g and 4□ for 3 hours by using a Type 90ti rotor to remove a supernatant, and the agglomerated pellet was dissolved with phosphate-buffered saline (PBS), thereby obtaining vesicles.

100 μl of the extracellular vesicles isolated from the blood and urine according to the above-described method was boiled at 100□ to allow the internal DNA to come out of the lipid and then cooled on ice for 5 min. Next, the resulting vesicles were centrifuged at 10,000×g and 4□ for 30 minutes to remove the remaining suspension, only the supernatant was collected, and then the amount of DNA extracted was quantified using a NanoDrop sprectrophotometer. In addition, to verify whether bacteria-derived DNA was present in the extracted DNA, PCR was performed using 16s rDNA primers shown in Table 1 below.

TABLE 1

| Primer | | Sequence | SEQ ID NO. |
|---|---|---|---|
| 16S rDNA | 16S_V3_F | 5'-TCGTCGGCAGCGTC AGATGTGTATAAGAG ACAGCCTACGGGNGG CWGCAG-3' | 1 |
| | 16S_V4_R | 5'-GTCTCGTGGGCTCG GAGATGTGTATAAGA GACAGGACTACHVGG GTATCTAATCC-3' | 2 |

Example 3 Metagenomic Analysis Using DNA Extracted from Blood and Urine

DNA was extracted using the same method as that used in Example 2, and then PCR was performed thereon using 16S rDNA primers shown in Table 1 to amplify DNA, followed by sequencing (Illumina MiSeq sequencer). The results were output as standard flowgram format (SFF) files, and the SFF files were converted into sequence files (.fasta) and nucleotide quality score files using GS FLX software (v2.9), and then credit rating for reads was identified, and portions with a window (20 bps) average base call accuracy of less than 99% (Phred score <20) were removed. After removing the low-quality portions, only reads having a length of 300 bps or more were used (Sickle version 1.33), and, for operational taxonomy unit (OTU) analysis, clustering was performed using UCLUST and USEARCH according to sequence similarity. In particular, clustering was performed based on sequence similarity values of 94% for genus, 90% for family, 85% for order, 80% for class, and 75% for phylum, and phylum, class, order, family, and genus levels of each OTU were classified, and bacteria with a sequence similarity of 97% or more were analyzed (QIIME) using 16S DNA sequence databases (108,453 sequences) of BLASTN and GreenGenes.

Example 4 Ovarian Cancer Diagnostic Model Based on Metagenomic Analysis of Bacteria-Derived EVs Isolated from Blood EVs were isolated from blood samples of 137 ovarian cancer patients and 139 normal individuals, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 2:
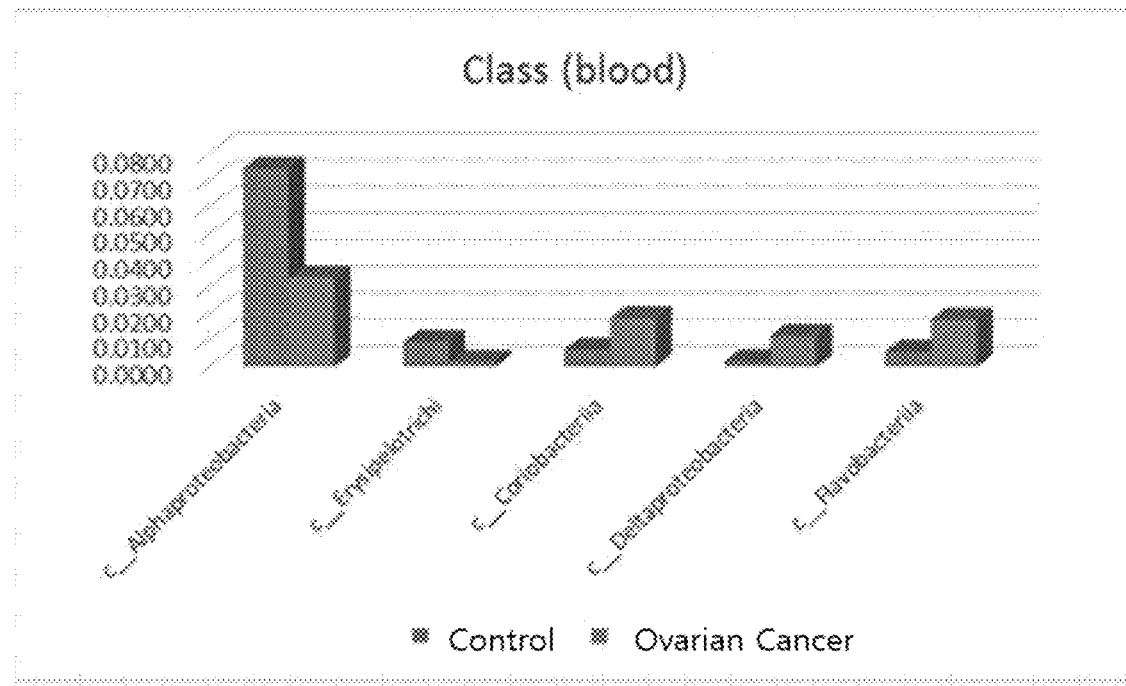
FIG. 2 shows the distribution of vesicles (extracellular vesicles; EVs) derived from bacteria, which is significant in diagnostic performance at a class level by isolating bacteria-derived vesicles from blood of a patient with ovarian cancer and normal individual, and then performing metagenomic analysis.
Figure 2:
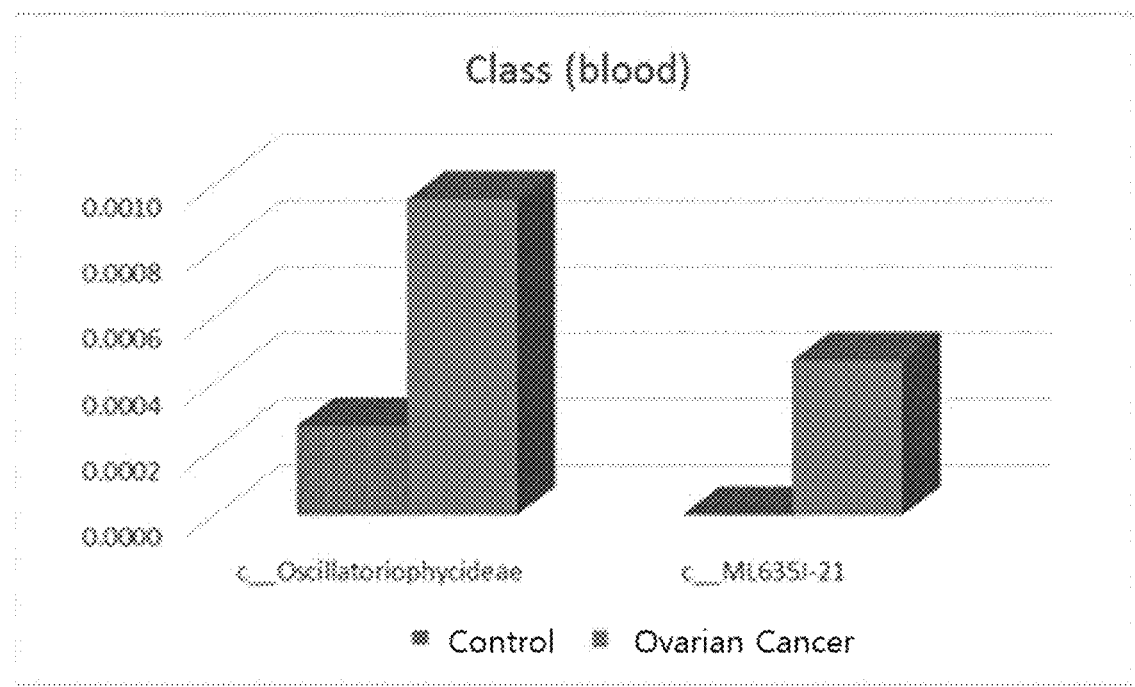

As a result of analyzing bacteria-derived EVs in blood at a class level, a diagnostic model developed using bacteria belonging to the class Erysipelotrichi, the class Alphaproteobacteria, the class Coriobacteriia, the class Flavobacteriia, the class Oscillatoriophycideae, the class Deltaproteobacteria, and the class ML635J-21 as a biomarker exhibited significant diagnostic performance for ovarian cancer (see Table 2 and FIG. 2).

TABLE 2

| name | Control | | Ovarian Cancer | | | | Training | | | Testing | | |
|---|---|---|---|---|---|---|---|---|---|---|---|---|
| | Mean | SD | Mean | SD | p value | Ratio | AUC | sensitivity | specificity | AUC | sensitivity | specificity |
| c_Erysipelotrichi | 0.0094 | 0.0136 | 0.0019 | 0.0026 | 0.0000 | 0.20 | 0.69 | 0.82 | 0.54 | 0.68 | 0.80 | 0.54 |
| c_Alphaproteobacteria | 0.0744 | 0.0587 | 0.0334 | 0.0231 | 0.0000 | 0.45 | 0.72 | 0.80 | 0.58 | 0.71 | 0.80 | 0.57 |
| c_Coriobacteriia | 0.0064 | 0.0086 | 0.0183 | 0.0111 | 0.0000 | 2.84 | 0.83 | 0.75 | 0.80 | 0.83 | 0.75 | 0.79 |
| c_Flavobacteriia | 0.0057 | 0.0121 | 0.0177 | 0.0226 | 0.0000 | 3.08 | 0.74 | 0.53 | 0.82 | 0.71 | 0.50 | 0.80 |
| c_Oscillatoriophycideae | 0.0003 | 0.0019 | 0.0010 | 0.0037 | 0.0520 | 3.54 | 0.61 | 0.41 | 0.78 | 0.57 | 0.37 | 0.78 |
| c_Deltaproteobacteria | 0.0021 | 0.0086 | 0.0117 | 0.0110 | 0.0000 | 5.51 | 0.84 | 0.67 | 0.90 | 0.83 | 0.66 | 0.89 |
| c_ML635J-21 | 0.0000 | 0.0000 | 0.0005 | 0.0013 | 0.0000 | | 0.60 | 0.24 | 0.94 | 0.56 | 0.22 | 0.93 |

Figure 3:
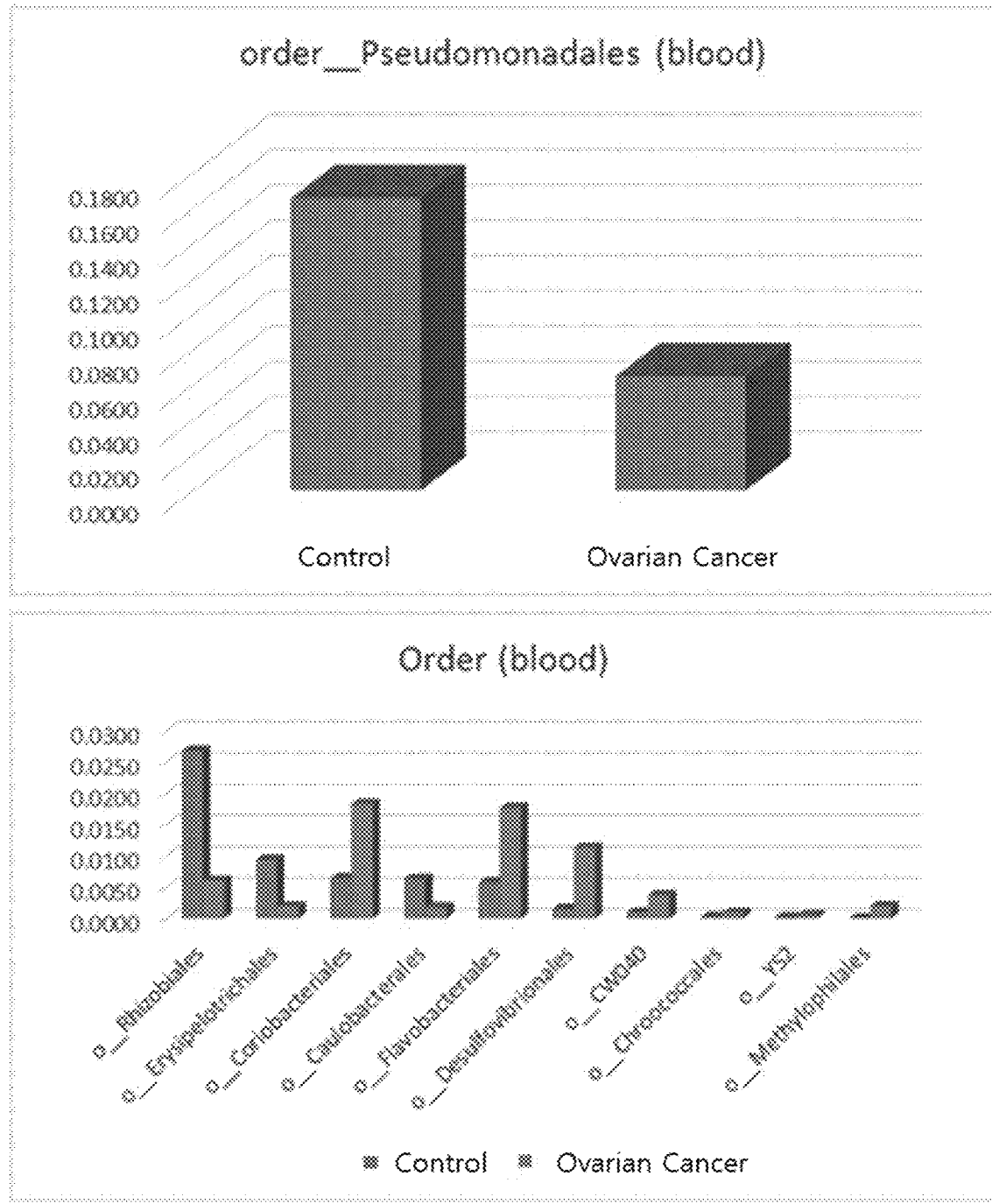
FIG. 3 shows the distribution of vesicles (extracellular vesicles; EVs) derived from bacteria, which is significant in diagnostic performance at an order level by isolating bacteria-derived vesicles from blood of a patient with ovarian cancer and normal individual, and then performing metagenomic analysis.

As a result of analyzing bacteria-derived EVs in blood at an order level, a diagnostic model developed using bacteria belonging to the order Erysipelotrichales, the order Rhizobiales, the order Caulobacterales, the order Pseudomonadales, the order Coriobacteriales, the order Flavobacteriales, the order YS2, the order Chroococcales, the order CW040, the order Desulfovibrionales, and the order Methylophilales as a biomarker exhibited significant diagnostic performance for ovarian cancer (see Table 3 and FIG. 3).

TABLE 3

| name | Control Mean | SD | Ovarian Cancer Mean | SD | p value | Ratio | Training AUC | sensitivity | specificity | Testing AUC | sensitivity | specificity |
|---|---|---|---|---|---|---|---|---|---|---|---|---|
| o_Erysipelotrichales | 0.0094 | 0.0136 | 0.0019 | 0.0026 | 0.0000 | 0.20 | 0.69 | 0.81 | 0.54 | 0.67 | 0.79 | 0.54 |
| o_Rhizobiales | 0.0268 | 0.0319 | 0.0060 | 0.0052 | 0.0000 | 0.22 | 0.79 | 0.89 | 0.62 | 0.78 | 0.88 | 0.62 |
| o_Caulobacterales | 0.0064 | 0.0109 | 0.0017 | 0.0027 | 0.0000 | 0.27 | 0.62 | 0.80 | 0.42 | 0.60 | 0.80 | 0.41 |
| o_Pseudomonadales | 0.1657 | 0.1328 | 0.0647 | 0.0386 | 0.0000 | 0.39 | 0.79 | 0.84 | 0.60 | 0.78 | 0.83 | 0.60 |
| o_Coriobacteriales | 0.0064 | 0.0086 | 0.0183 | 0.0111 | 0.0000 | 2.84 | 0.83 | 0.74 | 0.79 | 0.82 | 0.74 | 0.79 |
| o_Flavobacteriales | 0.0057 | 0.0121 | 0.0177 | 0.0226 | 0.0000 | 3.08 | 0.74 | 0.53 | 0.82 | 0.72 | 0.51 | 0.82 |
| o_YS2 | 0.0002 | 0.0015 | 0.0005 | 0.0012 | 0.0266 | 3.38 | 0.61 | 0.38 | 0.81 | 0.56 | 0.36 | 0.76 |
| o_Chroococcales | 0.0003 | 0.0018 | 0.0009 | 0.0037 | 0.0574 | 3.52 | 0.60 | 0.42 | 0.75 | 0.54 | 0.38 | 0.71 |
| o_CW040 | 0.0010 | 0.0056 | 0.0038 | 0.0044 | 0.0000 | 3.92 | 0.76 | 0.56 | 0.91 | 0.75 | 0.53 | 0.91 |
| o_Desulfovibrionales | 0.0015 | 0.0084 | 0.0113 | 0.0109 | 0.0000 | 7.37 | 0.86 | 0.69 | 0.93 | 0.86 | 0.70 | 0.93 |
| o_Methylophilales | 0.0000 | 0.0002 | 0.0020 | 0.0035 | 0.0000 | 95.25 | 0.76 | 0.49 | 0.98 | 0.72 | 0.49 | 0.98 |

Figure 4:
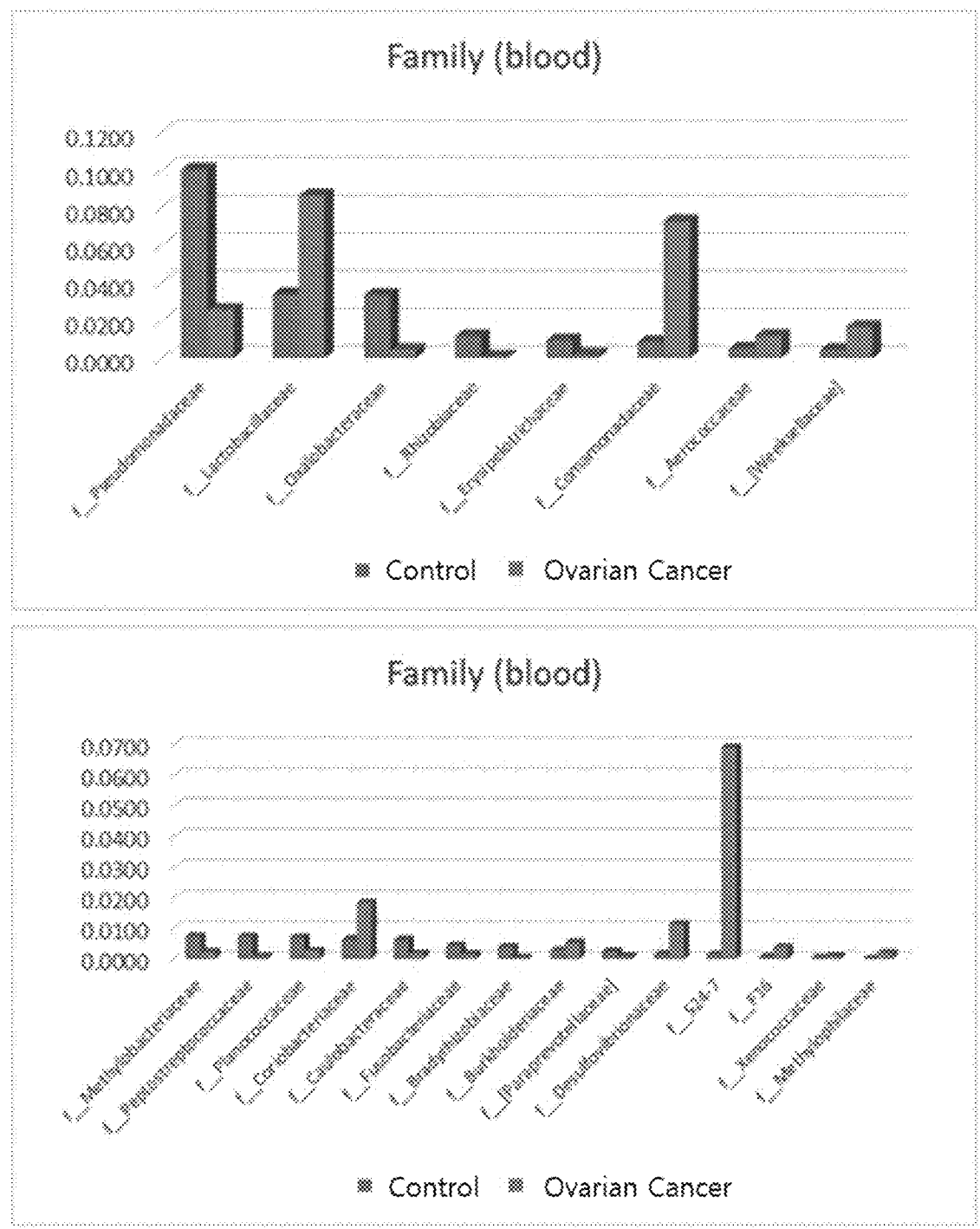
FIG. 4 shows the distribution of vesicles (extracellular vesicles; EVs) derived from bacteria, which is significant in diagnostic performance at a family level by isolating bacteria-derived vesicles from blood of a patient with ovarian cancer and normal individual, and then performing metagenomic analysis.

As a result of analyzing bacteria-derived EVs in blood at a family level, a diagnostic model developed using bacteria belonging to the family Rhizobiaceae, the family Bradyrhizobiaceae, the family Peptostreptococcaceae, the family Oxalobacteraceae, the family Erysipelotrichaceae, the family Pseudomonadaceae, the family Caulobacteraceae, the family Methylobacteriaceae, the family Paraprevotellaceae, the family Fusobacteriaceae, the family Planococcaceae, the family Burkholderiaceae, the family Aerococcaceae, the family Lactobacillaceae, the family Coriobacteriaceae, the family Weeksellaceae, the family Xenococcaceae, the family F16, the family Desulfovibrionaceae, the family Comamonadaceae, the family S24-7, and the family Methylophilaceae as a biomarker exhibited significant diagnostic performance for ovarian cancer (see Table 4 and FIG. 4).

TABLE 4

| name | Control Mean | SD | Ovarian Cancer Mean | SD | p value | Ratio | Training AUC | sensitivity | specificity | Testing AUC | sensitivity | specificity |
|---|---|---|---|---|---|---|---|---|---|---|---|---|
| f_Rhizobiaceae | 0.0116 | 0.0237 | 0.0007 | 0.0019 | 0.0000 | 0.06 | 0.81 | 0.90 | 0.56 | 0.79 | 0.90 | 0.55 |
| f_Bradyrhizobiaceae | 0.0039 | 0.0119 | 0.0003 | 0.0010 | 0.0005 | 0.09 | 0.67 | 0.87 | 0.38 | 0.63 | 0.85 | 0.37 |
| f_Peptostreptococcaceae | 0.0073 | 0.0191 | 0.0007 | 0.0016 | 0.0001 | 0.10 | 0.67 | 0.82 | 0.43 | 0.66 | 0.81 | 0.42 |
| f_Oxalobacteraceae | 0.0335 | 0.0482 | 0.0043 | 0.0127 | 0.0000 | 0.13 | 0.81 | 0.93 | 0.62 | 0.80 | 0.92 | 0.61 |
| f_Erysipelotrichaceae | 0.0094 | 0.0136 | 0.0019 | 0.0026 | 0.0000 | 0.20 | 0.69 | 0.82 | 0.54 | 0.67 | 0.80 | 0.54 |
| f_Pseudomonadaceae | 0.1001 | 0.1087 | 0.0256 | 0.0186 | 0.0000 | 0.26 | 0.87 | 0.86 | 0.72 | 0.87 | 0.85 | 0.70 |
| f_Caulobacteraceae | 0.0064 | 0.0109 | 0.0017 | 0.0027 | 0.0000 | 0.27 | 0.62 | 0.80 | 0.42 | 0.61 | 0.79 | 0.41 |
| f_Methylobacteriaceae | 0.0074 | 0.0104 | 0.0023 | 0.0030 | 0.0000 | 0.31 | 0.61 | 0.78 | 0.46 | 0.60 | 0.77 | 0.46 |
| f_[Paraprevotellaceae] | 0.0025 | 0.0051 | 0.0008 | 0.0018 | 0.0004 | 0.32 | 0.63 | 0.75 | 0.44 | 0.61 | 0.73 | 0.39 |
| f_Fusobacteriaceae | 0.0043 | 0.0085 | 0.0015 | 0.0029 | 0.0003 | 0.35 | 0.61 | 0.74 | 0.41 | 0.55 | 0.70 | 0.38 |
| f_Planococcaceae | 0.0070 | 0.0115 | 0.0026 | 0.0028 | 0.0000 | 0.37 | 0.64 | 0.73 | 0.45 | 0.62 | 0.71 | 0.46 |
| f_Burkholderiaceae | 0.0027 | 0.0070 | 0.0054 | 0.0057 | 0.0006 | 2.00 | 0.73 | 0.52 | 0.81 | 0.72 | 0.53 | 0.79 |
| f_Aerococcaceae | 0.0050 | 0.0097 | 0.0117 | 0.0107 | 0.0000 | 2.35 | 0.75 | 0.58 | 0.80 | 0.74 | 0.56 | 0.80 |
| f_Lactobacillaceae | 0.0340 | 0.0326 | 0.0863 | 0.0563 | 0.0000 | 2.54 | 0.81 | 0.65 | 0.83 | 0.80 | 0.63 | 0.84 |
| f_Coriobacteriaceae | 0.0064 | 0.0086 | 0.0183 | 0.0111 | 0.0000 | 2.84 | 0.83 | 0.74 | 0.79 | 0.82 | 0.74 | 0.79 |
| f_[Weeksellaceae] | 0.0044 | 0.0099 | 0.0165 | 0.0223 | 0.0000 | 3.74 | 0.75 | 0.51 | 0.84 | 0.74 | 0.52 | 0.83 |
| f_Xenococcaceae | 0.0002 | 0.0018 | 0.0009 | 0.0037 | 0.0428 | 4.15 | 0.61 | 0.41 | 0.78 | 0.58 | 0.40 | 0.75 |
| f_F16 | 0.0006 | 0.0029 | 0.0037 | 0.0044 | 0.0000 | 6.20 | 0.79 | 0.56 | 0.92 | 0.75 | 0.56 | 0.92 |
| f_Desulfovibrionaceae | 0.0015 | 0.0084 | 0.0113 | 0.0109 | 0.0000 | 7.37 | 0.86 | 0.69 | 0.93 | 0.86 | 0.69 | 0.93 |
| f_Comamonadaceae | 0.0085 | 0.0154 | 0.0727 | 0.0802 | 0.0000 | 8.51 | 0.91 | 0.75 | 0.86 | 0.90 | 0.73 | 0.85 |
| f_S24-7 | 0.0014 | 0.0038 | 0.0689 | 0.0516 | 0.0000 | 49.83 | 0.97 | 0.89 | 0.96 | 0.98 | 0.87 | 0.96 |
| f_Methylophilaceae | 0.0000 | 0.0002 | 0.0020 | 0.0035 | 0.0000 | 95.25 | 0.75 | 0.49 | 0.98 | 0.72 | 0.49 | 0.98 |

Figure 5:
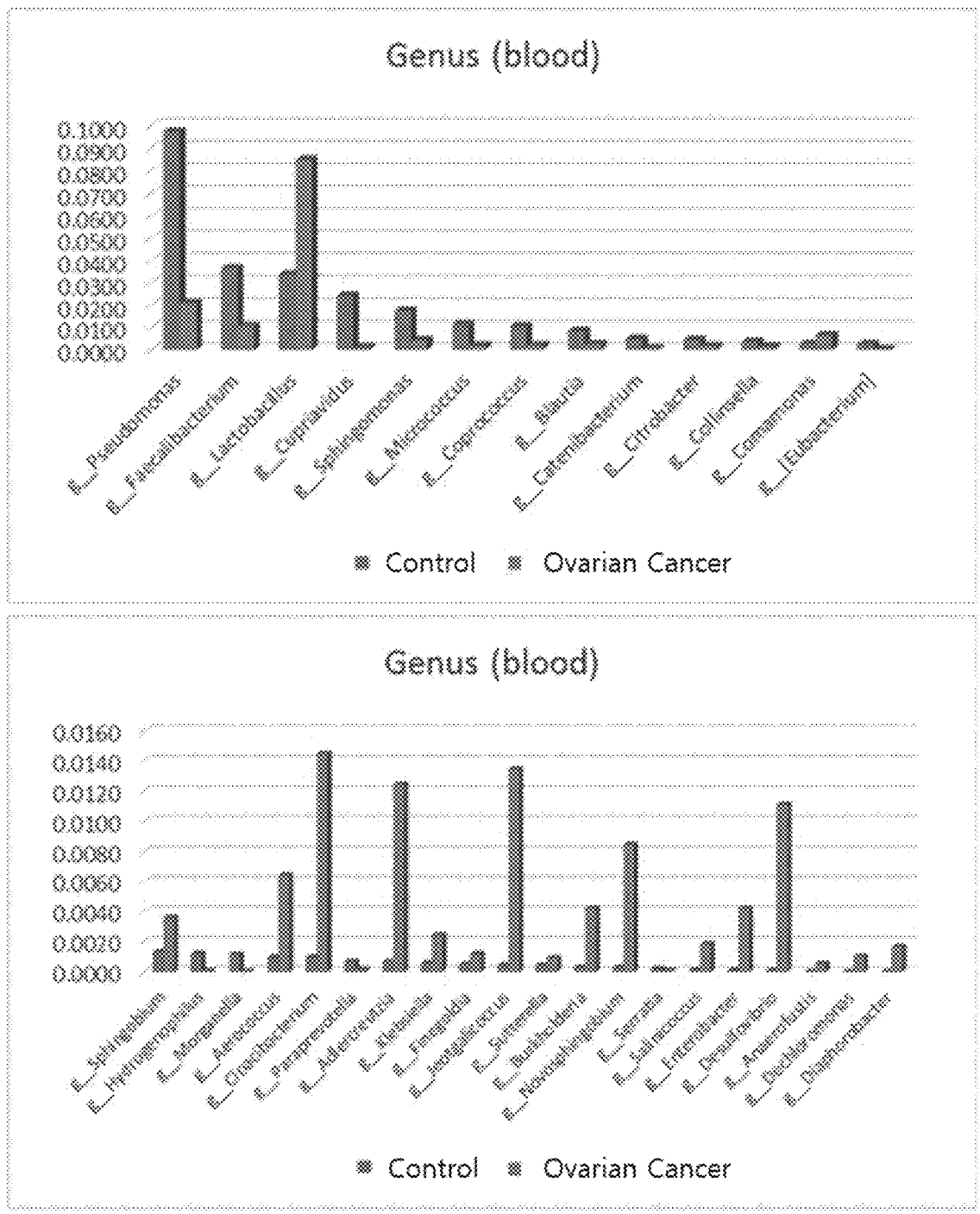
FIG. 5 shows the distribution of vesicles (extracellular vesicles; EVs) derived from bacteria, which is significant in diagnostic performance at a genus level by isolating bacteria-derived vesicles from blood of a patient with ovarian cancer and normal individual, and then performing metagenomic analysis.

As a result of analyzing bacteria-derived EVs in blood at a genus level, a diagnostic model developed using bacteria belonging to the genus *Morganella*, the genus *Hydrogenophilus*, the genus *Cupriavidus*, the genus *Eubacterium*, the genus *Catenibacterium*, the genus *Micrococcus*, the genus *Coprococcus*, the genus *Pseudomonas*, the genus *Paraprevotella*, the genus *Sphingomonas*, the genus *Faecalibacterium*, the genus *Blautia*, the genus *Serratia*, the genus *Citrobacter*, and the genus *Collinsella* as a biomarker exhibited significant diagnostic performance for ovarian cancer (see Table 5 and FIG. 5).

TABLE 5

| | Control | | Ovarian Cancer | | | | Training | | | Testing | | |
|---|---|---|---|---|---|---|---|---|---|---|---|---|
| | Mean | SD | Mean | SD | p value | Ratio | AUC | sensitivity | specificity | AUC | sensitivity | specificity |
| g_Morganella | 0.0012 | 0.0032 | 0.0000 | 0.0002 | 0.0000 | 0.02 | 0.66 | 0.95 | 0.29 | 0.64 | 0.94 | 0.28 |
| g_Hydrogenophilus | 0.0012 | 0.0048 | 0.0000 | 0.0003 | 0.0042 | 0.04 | 0.62 | 0.89 | 0.27 | 0.58 | 0.86 | 0.27 |
| g_Cupriavidus | 0.0242 | 0.0432 | 0.0011 | 0.0017 | 0.0000 | 0.04 | 0.75 | 0.90 | 0.55 | 0.73 | 0.90 | 0.55 |
| g_[Eubacterium] | 0.0026 | 0.0055 | 0.0003 | 0.0008 | 0.0000 | 0.11 | 0.68 | 0.86 | 0.41 | 0.65 | 0.86 | 0.40 |
| g_Catenibacterium | 0.0050 | 0.0105 | 0.0007 | 0.0015 | 0.0000 | 0.13 | 0.68 | 0.82 | 0.44 | 0.68 | 0.81 | 0.44 |
| g_Micrococcus | 0.0115 | 0.0185 | 0.0019 | 0.0034 | 0.0000 | 0.17 | 0.66 | 0.84 | 0.44 | 0.64 | 0.83 | 0.43 |
| g_Coprococcus | 0.0105 | 0.0141 | 0.0022 | 0.0029 | 0.0000 | 0.21 | 0.67 | 0.81 | 0.50 | 0.66 | 0.79 | 0.48 |
| g_Pseudomonas | 0.0976 | 0.1087 | 0.0209 | 0.0142 | 0.0000 | 0.21 | 0.89 | 0.88 | 0.75 | 0.89 | 0.87 | 0.74 |
| g_Paraprevotella | 0.0007 | 0.0024 | 0.0002 | 0.0007 | 0.0174 | 0.24 | 0.62 | 0.81 | 0.33 | 0.58 | 0.79 | 0.30 |
| g_Sphingomonas | 0.0176 | 0.0240 | 0.0043 | 0.0043 | 0.0000 | 0.25 | 0.73 | 0.81 | 0.55 | 0.72 | 0.79 | 0.54 |
| g_Faecalibacterium | 0.0364 | 0.0389 | 0.0106 | 0.0088 | 0.0000 | 0.29 | 0.69 | 0.83 | 0.56 | 0.68 | 0.81 | 0.55 |
| g_Blautia | 0.0084 | 0.0096 | 0.0025 | 0.0034 | 0.0000 | 0.30 | 0.67 | 0.80 | 0.53 | 0.65 | 0.78 | 0.52 |
| g_Serratia | 0.0002 | 0.0007 | 0.0001 | 0.0004 | 0.0451 | 0.36 | 0.63 | 0.79 | 0.37 | 0.59 | 0.74 | 0.33 |
| g_Citrobacter | 0.0045 | 0.0064 | 0.0016 | 0.0024 | 0.0000 | 0.36 | 0.65 | 0.77 | 0.49 | 0.63 | 0.76 | 0.48 |
| g_Collinsella | 0.0037 | 0.0059 | 0.0015 | 0.0027 | 0.0001 | 0.40 | 0.62 | 0.76 | 0.46 | 0.59 | 0.74 | 0.45 |
| g_Sutterella | 0.0005 | 0.0025 | 0.0009 | 0.0018 | 0.0807 | 2.00 | 0.61 | 0.46 | 0.74 | 0.55 | 0.42 | 0.71 |
| g_Finegoldia | 0.0005 | 0.0029 | 0.0012 | 0.0020 | 0.0251 | 2.27 | 0.65 | 0.48 | 0.78 | 0.61 | 0.46 | 0.75 |
| g_Comamonas | 0.0027 | 0.0076 | 0.0066 | 0.0091 | 0.0001 | 2.49 | 0.70 | 0.49 | 0.84 | 0.67 | 0.46 | 0.85 |
| g_Lactobacillus | 0.0337 | 0.0324 | 0.0849 | 0.0568 | 0.0000 | 2.52 | 0.80 | 0.64 | 0.83 | 0.79 | 0.62 | 0.83 |
| g_Sphingobium | 0.0013 | 0.0058 | 0.0036 | 0.0054 | 0.0009 | 2.70 | 0.72 | 0.49 | 0.84 | 0.69 | 0.48 | 0.84 |
| g_Klebsiella | 0.0006 | 0.0016 | 0.0024 | 0.0039 | 0.0000 | 4.12 | 0.71 | 0.47 | 0.86 | 0.70 | 0.46 | 0.86 |
| g_Aerococcus | 0.0010 | 0.0055 | 0.0064 | 0.0085 | 0.0000 | 6.54 | 0.82 | 0.59 | 0.94 | 0.79 | 0.57 | 0.95 |
| g_Burkholderia | 0.0003 | 0.0019 | 0.0042 | 0.0048 | 0.0000 | 13.77 | 0.90 | 0.77 | 0.95 | 0.89 | 0.76 | 0.95 |
| g_Cloacibacterium | 0.0010 | 0.0062 | 0.0145 | 0.0207 | 0.0000 | 14.79 | 0.87 | 0.63 | 0.95 | 0.86 | 0.63 | 0.94 |
| g_Salinicoccus | 0.0001 | 0.0008 | 0.0019 | 0.0024 | 0.0000 | 16.53 | 0.80 | 0.59 | 0.97 | 0.77 | 0.58 | 0.98 |
| g_Adlercreutzia | 0.0007 | 0.0020 | 0.0124 | 0.0093 | 0.0000 | 18.55 | 0.92 | 0.82 | 0.94 | 0.91 | 0.80 | 0.94 |
| g_Jeotgalicoecus | 0.0005 | 0.0018 | 0.0135 | 0.0150 | 0.0000 | 28.95 | 0.92 | 0.80 | 0.95 | 0.91 | 0.80 | 0.95 |
| g_Novosphingobium | 0.0003 | 0.0014 | 0.0084 | 0.0119 | 0.0000 | 29.38 | 0.87 | 0.68 | 0.95 | 0.87 | 0.67 | 0.95 |
| g_Enterobacter | 0.0001 | 0.0003 | 0.0042 | 0.0060 | 0.0000 | 40.30 | 0.80 | 0.62 | 0.94 | 0.76 | 0.61 | 0.94 |
| g_Anaerofustis | 0.0000 | 0.0001 | 0.0006 | 0.0014 | 0.0000 | 64.74 | 0.63 | 0.28 | 0.95 | 0.59 | 0.27 | 0.93 |
| g_Desulfovibrio | 0.0001 | 0.0004 | 0.0111 | 0.0109 | 0.0000 | 110.89 | 0.90 | 0.79 | 0.97 | 0.90 | 0.79 | 0.97 |
| g_Dechloromonas | 0.0000 | 0.0001 | 0.0010 | 0.0023 | 0.0000 | 129.91 | 0.66 | 0.32 | 0.98 | 0.64 | 0.32 | 0.98 |
| g_Diaphorobacter | 0.0000 | 0.0000 | 0.0017 | 0.0023 | 0.0000 | 1769.58 | 0.84 | 0.65 | 0.99 | 0.80 | 0.64 | 0.98 |

Example 5 Ovarian Cancer Diagnostic Model Based on Metagenomic Analysis of Bacteria-Derived EVs Isolated from Urine EVs were isolated from urine samples of 135 ovarian cancer patients and 136 normal individuals, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 6:
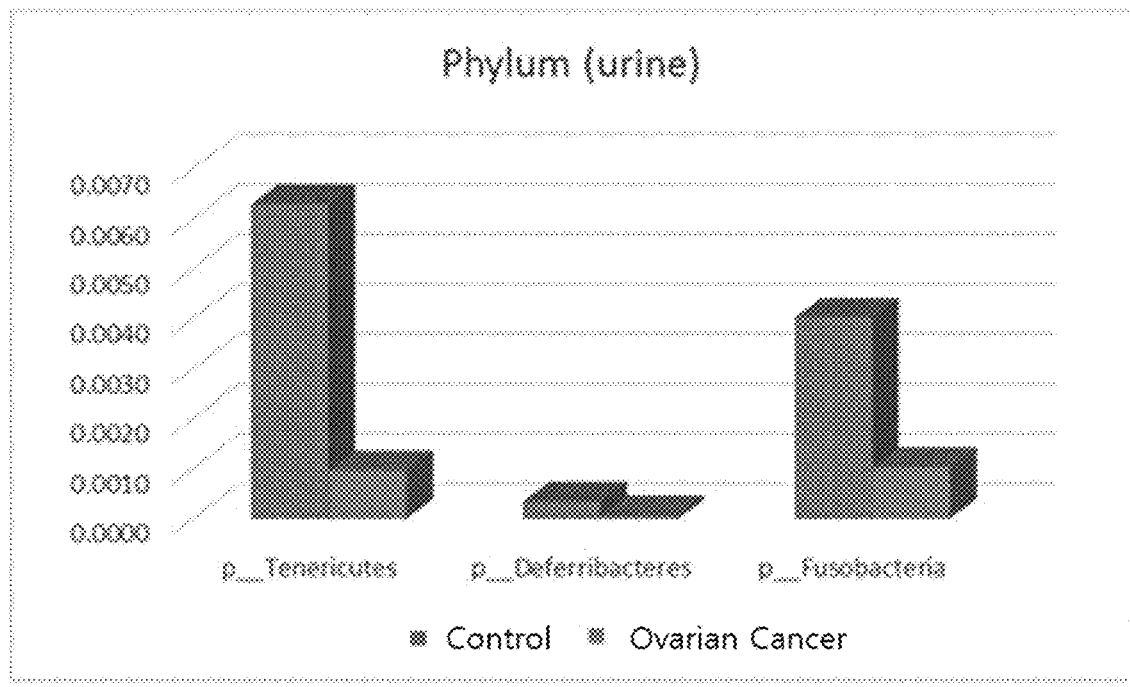
FIG. 6 shows the distribution of vesicles (extracellular vesicles; EVs) derived from bacteria, which is significant in diagnostic performance at a phylum level by isolating bacteria-derived vesicles from urine of a patient with ovarian cancer and normal individual, and then performing metagenomic analysis.
Figure 6:
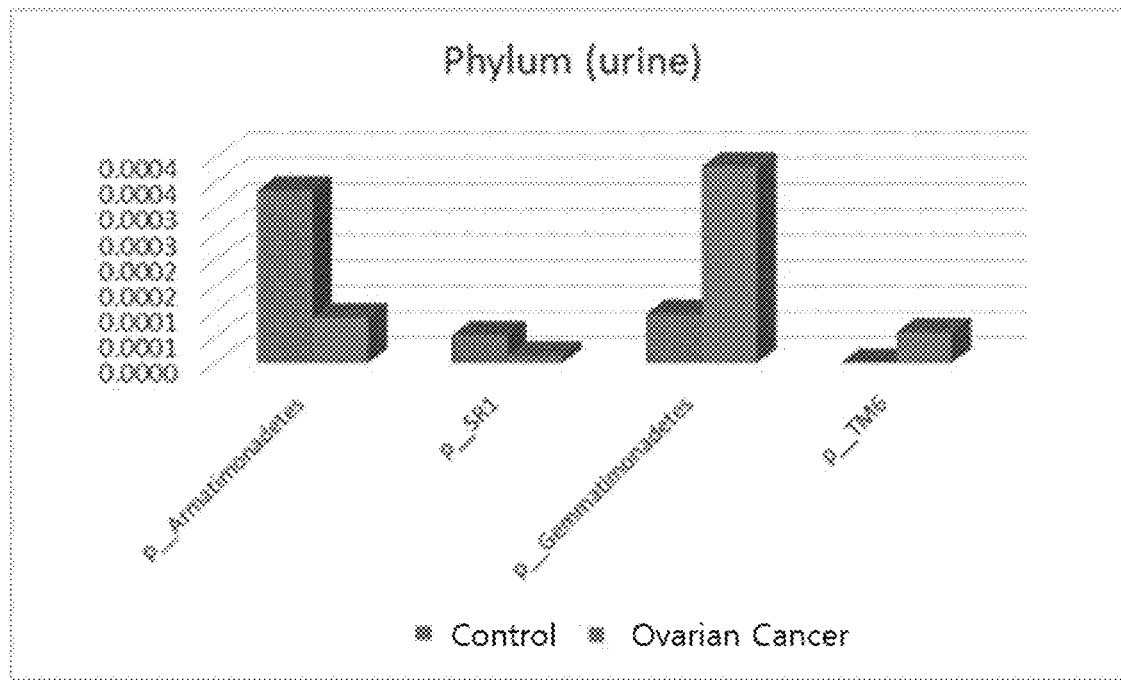

As a result of analyzing bacteria-derived EVs in urine at a phylum level, a diagnostic model developed using bacteria belonging to the phylum Tenericutes, the phylum Deferribacteres, the phylum Fusobacteria, the phylum Armatimonadetes, the phylum SR1, the phylum Gemmatimonadetes, and the phylum TM6 as a biomarker exhibited significant diagnostic performance for ovarian cancer (see Table 6 and FIG. 6).

TABLE 6

| | Control | | Ovarian Cancer | | | | Training | | | Testing | | |
|---|---|---|---|---|---|---|---|---|---|---|---|---|
| name | Mean | SD | Mean | SD | p value | Ratio | AUC | sensitivity | specificity | AUC | sensitivity | specificity |
| p_Tenericutes | 0.0063 | 0.0086 | 0.0010 | 0.0022 | 0.0000 | 0.15 | 0.79 | 0.80 | 0.59 | 0.78 | 0.79 | 0.59 |
| p_Deferribacteres | 0.0003 | 0.0008 | 0.0001 | 0.0004 | 0.0004 | 0.17 | 0.68 | 0.76 | 0.50 | 0.67 | 0.75 | 0.49 |
| p_Fusobacteria | 0.0040 | 0.0057 | 0.0010 | 0.0023 | 0.0000 | 0.26 | 0.74 | 0.84 | 0.54 | 0.73 | 0.80 | 0.53 |
| p_Armatimonadetes | 0.0003 | 0.0008 | 0.0001 | 0.0004 | 0.0025 | 0.26 | 0.63 | 0.72 | 0.46 | 0.62 | 0.70 | 0.46 |
| p_SR1 | 0.0001 | 0.0003 | 0.0000 | 0.0002 | 0.1834 | 0.27 | 0.61 | 0.65 | 0.49 | 0.61 | 0.65 | 0.48 |
| p_Gemmatimonadetes | 0.0001 | 0.0004 | 0.0004 | 0.0012 | 0.0085 | 3.99 | 0.61 | 0.53 | 0.63 | 0.61 | 0.52 | 0.61 |
| p_TM6 | 0.0000 | 0.0000 | 0.0001 | 0.0003 | 0.0236 | | 0.60 | 0.55 | 0.58 | 0.60 | 0.56 | 0.57 |

Figure 7:
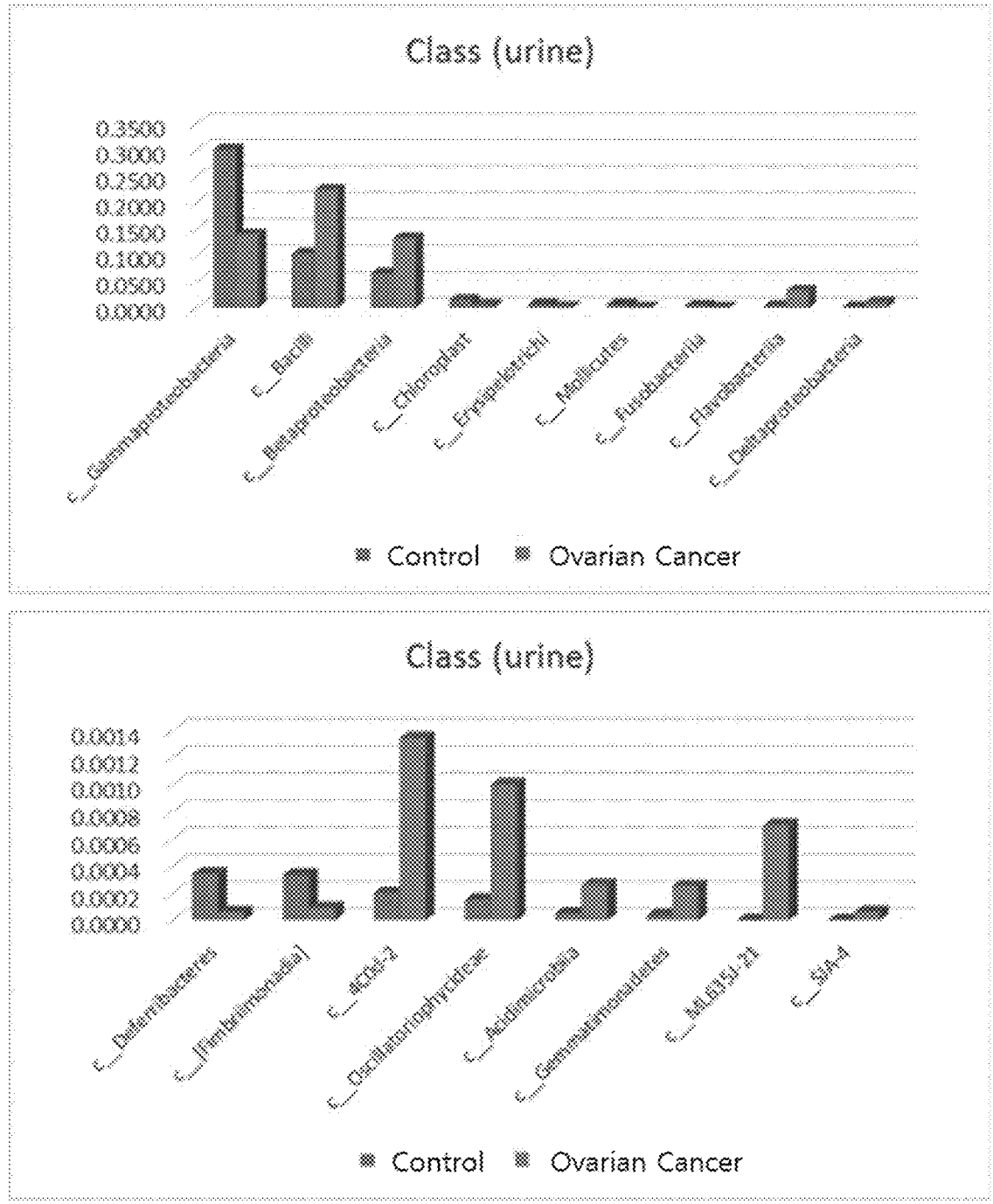
FIG. 7 shows the distribution of vesicles (extracellular vesicles; EVs) derived from bacteria, which is significant in diagnostic performance at a class level by isolating bacteria-derived vesicles from urine of a patient with ovarian cancer and normal individual, and then performing metagenomic analysis.

As a result of analyzing bacteria-derived EVs in urine at a class level, a diagnostic model developed using bacteria belonging to the class Mollicutes, the class Deferribacteres, the class Fusobacteriia, the class Fimbriimonadia, the class Erysipelotrichi, the class Chloroplast, the class Gammaproteobacteria, the class Betaproteobacteria, the class Bacilli, the class Acidimicrobiia, the class Deltaproteobacteria, the class Oscillatoriophycideae, the class 4C0d-2, the class Gemmatimonadetes, the class Flavobacteriia, the class ML635J-21, and the class SJA-4 as a biomarker exhibited significant diagnostic performance for ovarian cancer (see Table 7 and FIG. 7).

les, the order Halanaerobiales, the order RF39, the order Deferribacterales, the order Pirellulales, the order Fusobacteriales, the order Fimbriimonadales, the order Erysipelotrichales, the order Pseudomonadales, the order Streptophyta, the order Turicibacterales, the order Burkholderiales, the order Sphingomonadales, the order Myxococcales, the order Thermales, the order YS2, the order Bacillales, the order Acidimicrobiales, the order Oceanospirillales, the order Legionellales, the order iii1-15, the order Chroococcales, the order CW040, the order EW055, the order Gemmatimonadales, the order Flavobac-

TABLE 7

| | Control | | Ovarian Cancer | | | | Training | | | Testing | | |
|---|---|---|---|---|---|---|---|---|---|---|---|---|
| name | Mean | SD | Mean | SD | p value | Ratio | AUC | sensitivity | specificity | AUC | sensitivity | specificity |
| c_Mollicutes | 0.0063 | 0.0086 | 0.0010 | 0.0022 | 0.0000 | 0.15 | 0.79 | 0.80 | 0.60 | 0.78 | 0.78 | 0.58 |
| c_Deferribacteres | 0.0003 | 0.0008 | 0.0001 | 0.0004 | 0.0004 | 0.17 | 0.68 | 0.75 | 0.52 | 0.67 | 0.74 | 0.50 |
| c_Fusobacteriia | 0.0040 | 0.0057 | 0.0010 | 0.0023 | 0.0000 | 0.26 | 0.74 | 0.83 | 0.54 | 0.73 | 0.81 | 0.51 |
| c_[Fimbriimonadia] | 0.0003 | 0.0008 | 0.0001 | 0.0004 | 0.0025 | 0.26 | 0.63 | 0.69 | 0.48 | 0.62 | 0.69 | 0.47 |
| c_Erysipelotrichi | 0.0067 | 0.0113 | 0.0018 | 0.0032 | 0.0000 | 0.27 | 0.78 | 0.80 | 0.57 | 0.77 | 0.80 | 0.57 |
| c_Chloroplast | 0.0147 | 0.0318 | 0.0054 | 0.0065 | 0.0010 | 0.37 | 0.63 | 0.71 | 0.46 | 0.62 | 0.71 | 0.46 |
| c_Gammaproteobacteria | 0.3013 | 0.1828 | 0.1392 | 0.0497 | 0.0000 | 0.46 | 0.81 | 0.90 | 0.70 | 0.81 | 0.89 | 0.70 |
| c_Betaproteobacteria | 0.0653 | 0.1524 | 0.1323 | 0.1238 | 0.0001 | 2.03 | 0.73 | 0.63 | 0.74 | 0.73 | 0.61 | 0.76 |
| c_Bacilli | 0.1031 | 0.0551 | 0.2242 | 0.1162 | 0.0000 | 2.17 | 0.83 | 0.74 | 0.85 | 0.83 | 0.74 | 0.85 |
| c_Acidimicrobiia | 0.0001 | 0.0002 | 0.0003 | 0.0008 | 0.0028 | 5.11 | 0.62 | 0.53 | 0.63 | 0.61 | 0.52 | 0.61 |
| c_Deltaproteobacteria | 0.0016 | 0.0026 | 0.0104 | 0.0115 | 0.0000 | 6.49 | 0.85 | 0.71 | 0.87 | 0.85 | 0.70 | 0.86 |
| c_Oscillatoriophycideae | 0.0002 | 0.0007 | 0.0010 | 0.0026 | 0.0003 | 6.61 | 0.64 | 0.49 | 0.69 | 0.64 | 0.49 | 0.68 |
| c_4C0d-2 | 0.0002 | 0.0005 | 0.0013 | 0.0027 | 0.0000 | 6.68 | 0.67 | 0.44 | 0.76 | 0.67 | 0.43 | 0.75 |
| c_Gemmatimonadetes | 0.0000 | 0.0002 | 0.0003 | 0.0009 | 0.0064 | 6.81 | 0.61 | 0.54 | 0.60 | 0.61 | 0.54 | 0.60 |
| c_Flavobacteriia | 0.0034 | 0.0053 | 0.0325 | 0.0406 | 0.0000 | 9.68 | 0.87 | 0.68 | 0.88 | 0.87 | 0.68 | 0.87 |
| c_ML635J-21 | 0.0000 | 0.0000 | 0.0007 | 0.0023 | 0.0006 | 610.44 | 0.64 | 0.47 | 0.73 | 0.64 | 0.46 | 0.73 |
| c_SJA-4 | 0.0000 | 0.0000 | 0.0001 | 0.0003 | 0.0236 | | 0.60 | 0.55 | 0.59 | 0.60 | 0.54 | 0.58 |

Figure 8:
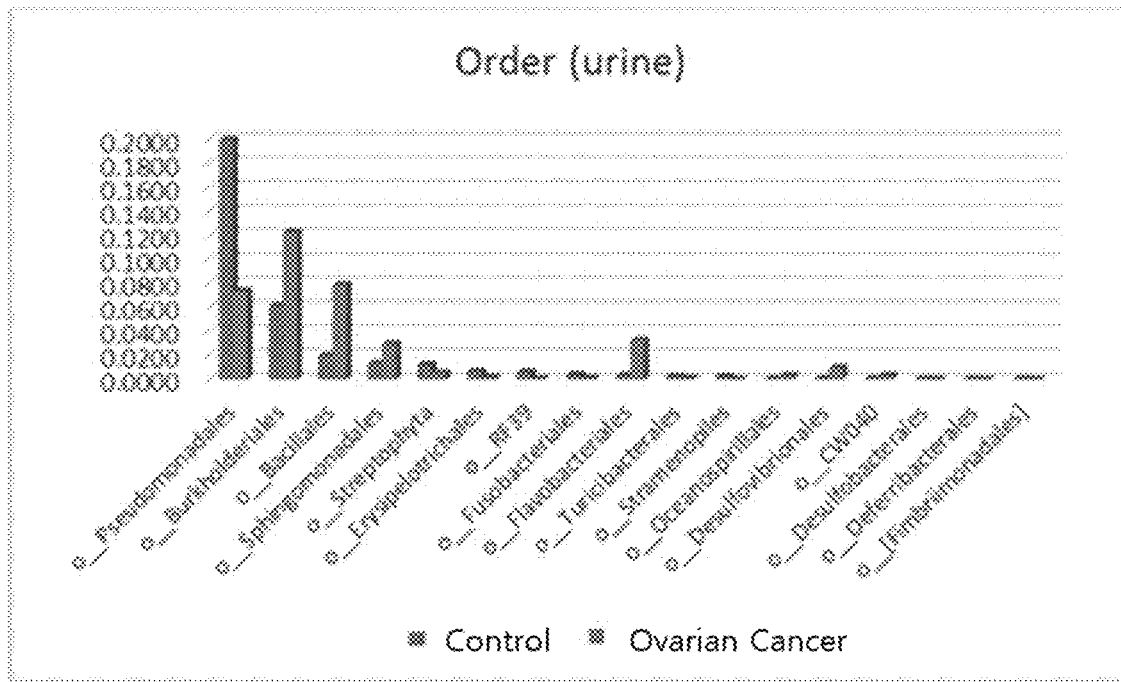
FIG. 8 shows the distribution of vesicles (extracellular vesicles; EVs) derived from bacteria, which is significant in diagnostic performance at an order level by isolating bacteria-derived vesicles from urine of a patient with ovarian cancer and normal individual, and then performing metagenomic analysis.
Figure 8:
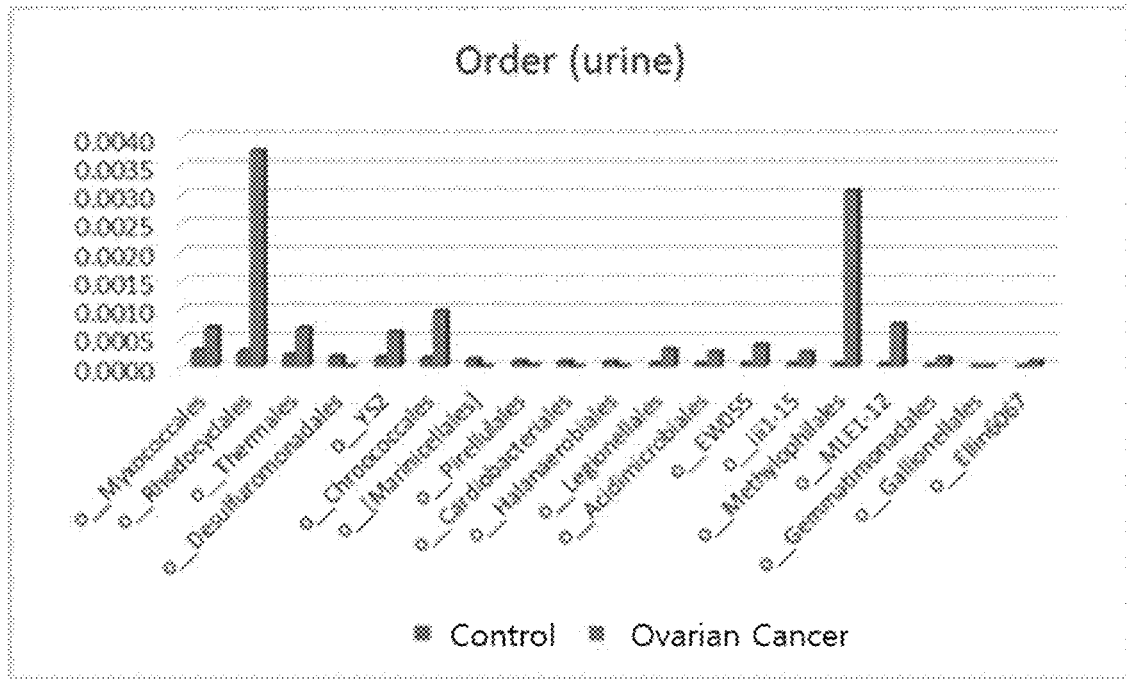

As a result of analyzing bacteria-derived EVs in urine at an order level, a diagnostic model developed using bacteria belonging to the order Desulfuromonadales, the order Desulfobacterales, the order Gallionellales, the order Cardiobacteriales, the order Stramenopiles, the order Marinicellateriales, the order Rhodocyclales, the order Desulfovibrionales, the order MLE1-12, the order Methylophilales, and the order Ellin6067 as a biomarker exhibited significant diagnostic performance for ovarian cancer (see Table 8 and FIG. 8).

TABLE 8

| | Control | | Ovarian Cancer | | | | Training | | | Testing | | |
|---|---|---|---|---|---|---|---|---|---|---|---|---|
| name | Mean | SD | Mean | SD | p value | Ratio | AUC | sensitivity | specificity | AUC | sensitivity | specificity |
| o_Desulfuromonadales | 0.0002 | 0.0011 | 0.0000 | 0.0000 | 0.0604 | 0.00 | 0.62 | 0.80 | 0.36 | 0.62 | 0.78 | 0.36 |
| o_Desulfooacterales | 0.0004 | 0.0015 | 0.0000 | 0.0000 | 0.0076 | 0.00 | 0.62 | 0.79 | 0.38 | 0.59 | 0.78 | 0.35 |
| o_Gallionellales | 0.0000 | 0.0000 | 0.0000 | 0.0000 | 0.0248 | 0.00 | 0.61 | 0.65 | 0.47 | 0.61 | 0.65 | 0.47 |
| o_Cardiooacteriales | 0.0001 | 0.0004 | 0.0000 | 0.0000 | 0.0140 | 0.00 | 0.61 | 0.70 | 0.44 | 0.61 | 0.69 | 0.44 |
| o_Stramenopiles | 0.0025 | 0.0054 | 0.0000 | 0.0001 | 0.0000 | 0.00 | 0.71 | 0.97 | 0.38 | 0.67 | 0.96 | 0.37 |
| o_[Marinicellales] | 0.0001 | 0.0006 | 0.0000 | 0.0000 | 0.0113 | 0.02 | 0.61 | 0.71 | 0.43 | 0.62 | 0.71 | 0.42 |
| o_Halanaerobiales | 0.0001 | 0.0006 | 0.0000 | 0.0000 | 0.1615 | 0.03 | 0.60 | 0.66 | 0.47 | 0.60 | 0.65 | 0.46 |
| o_RF39 | 0.0062 | 0.0086 | 0.0006 | 0.0013 | 0.0000 | 0.10 | 0.81 | 0.83 | 0.63 | 0.81 | 0.83 | 0.61 |
| o_Deferribacterales | 0.0003 | 0.0008 | 0.0001 | 0.0004 | 0.0004 | 0.17 | 0.68 | 0.75 | 0.51 | 0.67 | 0.75 | 0.49 |
| o_Pirellulales | 0.0001 | 0.0004 | 0.0000 | 0.0003 | 0.1246 | 0.25 | 0.60 | 0.65 | 0.49 | 0.58 | 0.63 | 0.46 |
| o_Fusobacteriales | 0.0040 | 0.0057 | 0.0010 | 0.0023 | 0.0000 | 0.26 | 0.74 | 0.82 | 0.52 | 0.73 | 0.82 | 0.52 |
| o_[Fimbriimonadales] | 0.0003 | 0.0008 | 0.0001 | 0.0004 | 0.0025 | 0.26 | 0.63 | 0.70 | 0.46 | 0.62 | 0.70 | 0.46 |
| o_Erysipelotrichales | 0.0067 | 0.0113 | 0.0018 | 0.0032 | 0.0000 | 0.27 | 0.78 | 0.81 | 0.57 | 0.77 | 0.80 | 0.55 |
| o_Pseudomonadales | 0.1996 | 0.1591 | 0.0737 | 0.0327 | 0.0000 | 0.37 | 0.80 | 0.86 | 0.66 | 0.79 | 0.85 | 0.64 |
| o_Streptophyta | 0.0122 | 0.0298 | 0.0053 | 0.0065 | 0.0094 | 0.44 | 0.61 | 0.66 | 0.48 | 0.59 | 0.64 | 0.47 |
| o_Turicibacterales | 0.0025 | 0.0037 | 0.0011 | 0.0025 | 0.0004 | 0.45 | 0.65 | 0.69 | 0.52 | 0.65 | 0.68 | 0.50 |
| o_Burkholderiales | 0.0613 | 0.1532 | 0.1228 | 0.1157 | 0.0002 | 2.00 | 0.73 | 0.62 | 0.74 | 0.71 | 0.61 | 0.74 |
| o_Sphingomonadales | 0.0133 | 0.0146 | 0.0296 | 0.0274 | 0.0000 | 2.23 | 0.72 | 0.55 | 0.78 | 0.70 | 0.52 | 0.77 |
| o_Myxococcales | 0.0003 | 0.0008 | 0.0007 | 0.0021 | 0.0429 | 2.38 | 0.60 | 0.55 | 0.57 | 0.60 | 0.57 | 0.56 |
| o_Thermales | 0.0002 | 0.0010 | 0.0007 | 0.0017 | 0.0072 | 3.22 | 0.63 | 0.53 | 0.64 | 0.62 | 0.51 | 0.61 |
| o_YS2 | 0.0002 | 0.0004 | 0.0006 | 0.0021 | 0.0166 | 3.62 | 0.60 | 0.52 | 0.63 | 0.60 | 0.51 | 0.61 |
| o_Bacillales | 0.0202 | 0.0181 | 0.0789 | 0.0724 | 0.0000 | 3.91 | 0.87 | 0.70 | 0.86 | 0.86 | 0.69 | 0.85 |
| o_Acidimicrobiales | 0.0001 | 0.0002 | 0.0003 | 0.0008 | 0.0028 | 5.11 | 0.62 | 0.52 | 0.63 | 0.61 | 0.53 | 0.62 |
| o_Oceanospirillales | 0.0006 | 0.0028 | 0.0033 | 0.0051 | 0.0000 | 5.31 | 0.79 | 0.62 | 0.84 | 0.78 | 0.59 | 0.83 |
| o_Legionellales | 0.0001 | 0.0006 | 0.0003 | 0.0008 | 0.0041 | 5.48 | 0.65 | 0.54 | 0.68 | 0.65 | 0.52 | 0.68 |
| o_iii1-15 | 0.0000 | 0.0004 | 0.0003 | 0.0016 | 0.1425 | 5.67 | 0.60 | 0.59 | 0.54 | 0.60 | 0.59 | 0.56 |
| o_Chroococcales | 0.0002 | 0.0007 | 0.0010 | 0.0026 | 0.0004 | 6.44 | 0.63 | 0.48 | 0.69 | 0.63 | 0.48 | 0.69 |

TABLE 8-continued

| name | Control Mean | SD | Ovarian Cancer Mean | SD | p value | Ratio | Training AUC | sensitivity | specificity | Testing AUC | sensitivity | specificity |
|---|---|---|---|---|---|---|---|---|---|---|---|---|
| o_CW040 | 0.0005 | 0.0018 | 0.0035 | 0.0044 | 0.0000 | 6.49 | 0.78 | 0.59 | 0.85 | 0.78 | 0.59 | 0.85 |
| o_EW055 | 0.0000 | 0.0002 | 0.0004 | 0.0017 | 0.0299 | 7.63 | 0.60 | 0.59 | 0.55 | 0.60 | 0.57 | 0.55 |
| o_Gemmatimonadales | 0.0000 | 0.0001 | 0.0002 | 0.0007 | 0.0288 | 8.08 | 0.61 | 0.55 | 0.58 | 0.61 | 0.55 | 0.59 |
| o_Flavobacteriales | 0.0034 | 0.0053 | 0.0325 | 0.0406 | 0.0000 | 9.68 | 0.87 | 0.69 | 0.88 | 0.86 | 0.68 | 0.86 |
| o_Rhodocyclales | 0.0003 | 0.0007 | 0.0038 | 0.0056 | 0.0000 | 13.55 | 0.77 | 0.58 | 0.89 | 0.77 | 0.58 | 0.89 |
| o_Desulfovibrionales | 0.0006 | 0.0013 | 0.0096 | 0.0112 | 0.0000 | 15.98 | 0.90 | 0.75 | 0.91 | 0.89 | 0.74 | 0.92 |
| o_MLE1-12 | 0.0000 | 0.0002 | 0.0007 | 0.0016 | 0.0000 | 21.03 | 0.66 | 0.45 | 0.77 | 0.64 | 0.42 | 0.75 |
| o_Methylophilales | 0.0000 | 0.0003 | 0.0031 | 0.0043 | 0.0000 | 84.22 | 0.79 | 0.56 | 0.96 | 0.79 | 0.54 | 0.96 |
| o_Ellin6067 | 0.0000 | 0.0000 | 0.0001 | 0.0005 | 0.0299 | 113.57 | 0.61 | 0.60 | 0.54 | 0.60 | 0.60 | 0.54 |

Figure 9:
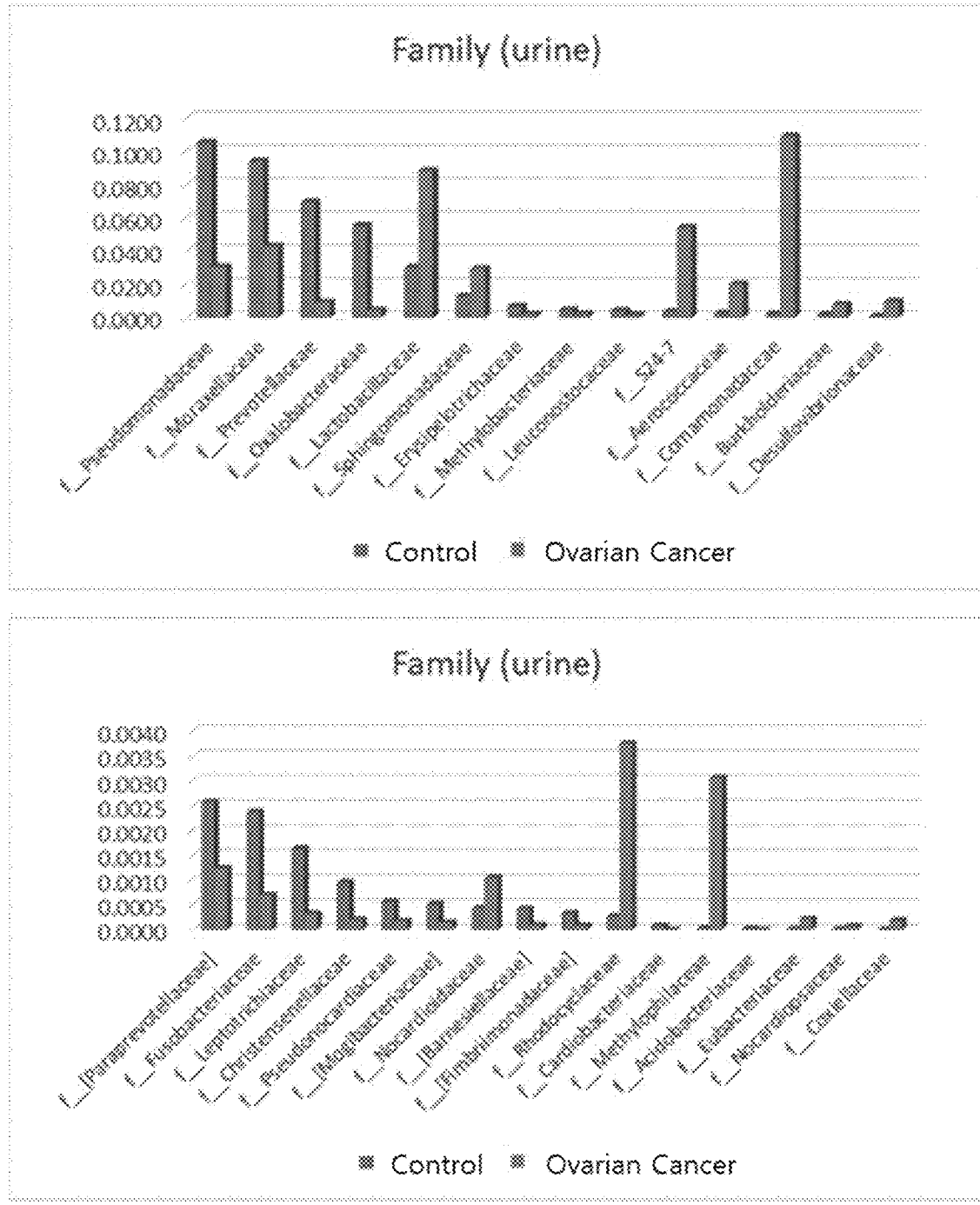
FIG. 9 shows the distribution of vesicles (extracellular vesicles; EVs) derived from bacteria, which is significant in diagnostic performance at a family level by isolating bacteria-derived vesicles from urine of a patient with ovarian cancer and normal individual, and then performing metagenomic analysis.

As a result of analyzing bacteria-derived EVs in urine at a family level, a diagnostic model developed using bacteria belonging to the family Cardiobacteriaceae, the family Acidobacteriaceae, the family Oxalobacteraceae, the family Prevotellaceae, the family Leptotrichiaceae, the family Chris tensenellaceae, the family Barnesiellaceae, the family Fimbriimonadaceae, the family Erysipelotrichaceae, the family Mogibacteriaceae, the family Pseudomonadaceae, the family Fusobacteriaceae, the family Pseudonocardiaceae, the family Leuconostocaceae, the family Moraxellaceae, the family Methylobacteriaceae, the family Paraprevotellaceae, the family Sphingomonadaceae, the family Nocardioidaceae, the family Lactobacillaceae, the family Burkholderiaceae, the family Aerococcaceae, the family Nocardiopsaceae, the family Rhodocyclaceae, the family S24-7, the family Eubacteriaceae, the family Des ulfovibrionaceae, the family Comamonadaceae, the family Methylophilaceae, and the family Coxiellaceae as a biomarker exhibited significant diagnostic performance for ovarian cancer (see Table 9 and FIG. 9).

As a result of analyzing bacteria-derived EVs in urine at a genus level, a diagnostic model developed using bacteria belonging to the genus *Morganella*, the genus *Rhizobium*, the genus *Exiguobacterium*, the genus *Cupriavidus*, the genus *Ralstonia*, the genus *Cellulomonas*, the genus *Sporosarcina*, the genus *Proteus*, the genus *Leptotrichia*, the genus SMB53, the genus *Prevotella*, the genus *Oribacterium*, the genus *Pediococcus*, the genus *Paraprevotella*, the genus *Methylobacterium*, the genus *Mucispirillum*, the genus *Catenibacterium*, the genus *Parabacteroides*, the genus *Collinsella*, the genus *Anaerostipes*, the genus *Pseudomonas*, the genus *Butyricimonas*, the genus *Fusobacterium*, the genus *Weissella*, the genus *Eubacterium*, the genus *Dialister*, the genus *Actinomyces*, the genus *Odoribacter*, the genus *Sphingomonas*, the genus *Bacteroides*, the genus *Turicibacter*, the genus *Enterococcus*, the genus *Dorea*, the genus *Lactobacillus*, the genus *Erwinia*, the genus *Staphylococcus*, the genus *Citrobacter*, the genus *Halomonas*, the genus *Sphingobium*, the genus *Gordonia*, the genus *Adlercreutzia*, the genus *Brevibacillus*, the genus *Aerococcus*, the

TABLE 9

Figure 10:
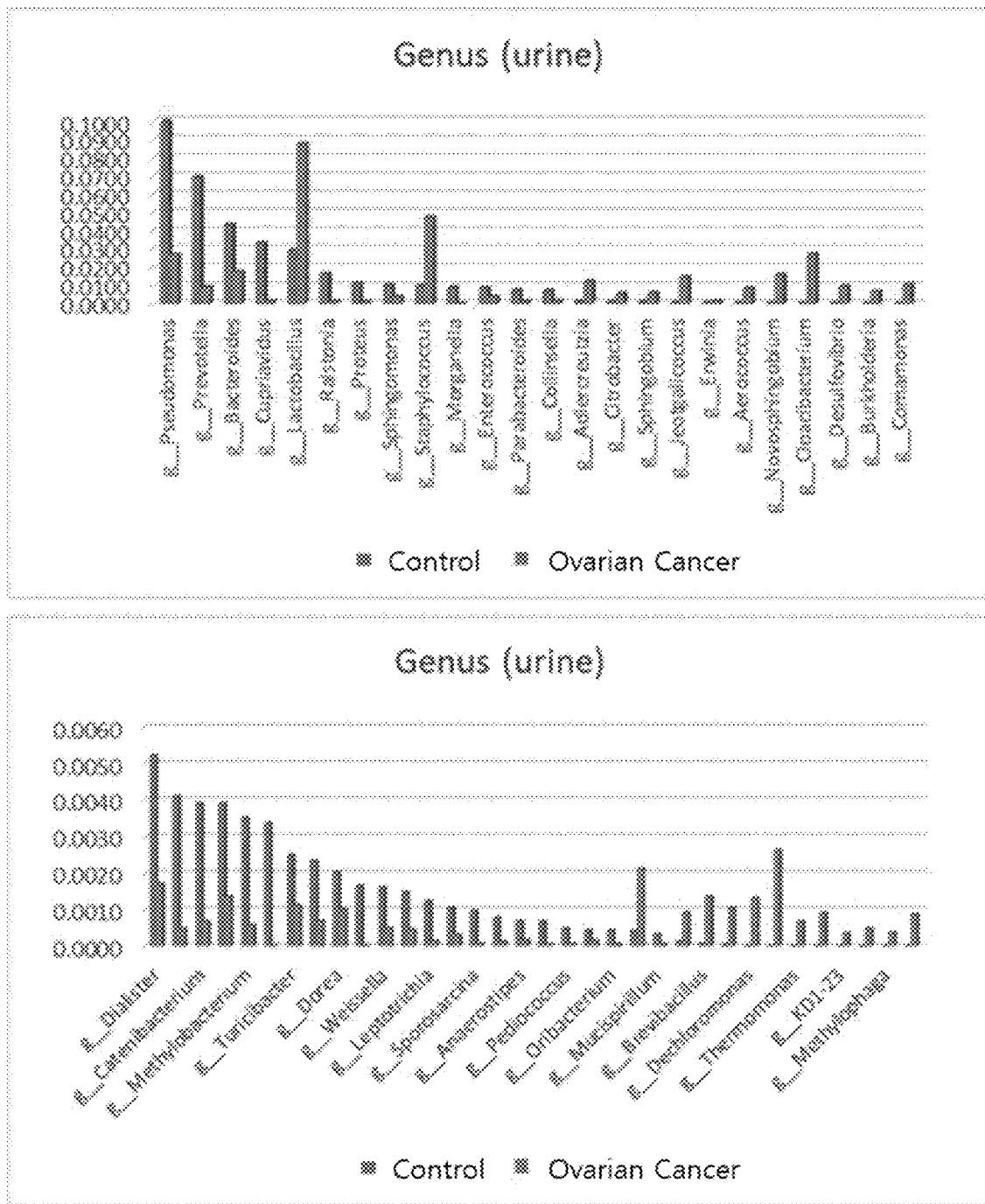
FIG. 10 shows the distribution of vesicles (extracellular vesicles; EVs) derived from bacteria, which is significant in diagnostic performance at a genus level by isolating bacteria-derived vesicles from urine of a patient with ovarian cancer and normal individual, and then performing metagenomic analysis.

| name | Control Mean | SD | Ovarian Cancer Mean | SD | p value | Ratio | Training AUC | sensitivity | specificity | Testing AUC | sensitivity | specificity |
|---|---|---|---|---|---|---|---|---|---|---|---|---|
| f_Cardiobacteriaceae | 0.0001 | 0.0017 | 0.0000 | 0.0013 | 0.0140 | 0.00 | 0.76 | 0.80 | 0.57 | 0.75 | 0.79 | 0.56 |
| f_Acidobacteriaceae | 0.0000 | 0.0007 | 0.0000 | 0.0005 | 0.0315 | 0.00 | 0.73 | 0.75 | 0.59 | 0.72 | 0.75 | 0.56 |
| f_Oxalobacteraceae | 0.0554 | 0.0027 | 0.0044 | 0.0051 | 0.0001 | 0.08 | 0.82 | 0.63 | 0.90 | 0.81 | 0.63 | 0.88 |
| f_Prevotellaceae | 0.0695 | 0.0131 | 0.0093 | 0.0684 | 0.0000 | 0.13 | 0.90 | 0.73 | 0.89 | 0.90 | 0.72 | 0.89 |
| f_Leptotrichiaceae | 0.0016 | 0.0059 | 0.0003 | 0.0031 | 0.0000 | 0.20 | 0.67 | 0.69 | 0.50 | 0.66 | 0.69 | 0.48 |
| f_Christensenellaceae | 0.0010 | 0.0023 | 0.0002 | 0.0019 | 0.0000 | 0.21 | 0.74 | 0.71 | 0.65 | 0.73 | 0.70 | 0.65 |
| f_[Barnesiellaceae] | 0.0004 | 0.0009 | 0.0001 | 0.0025 | 0.0064 | 0.23 | 0.68 | 0.48 | 0.81 | 0.68 | 0.48 | 0.79 |
| f_[Fimbriimonadaceae] | 0.0003 | 0.0022 | 0.0001 | 0.0002 | 0.0025 | 0.26 | 0.96 | 0.97 | 0.84 | 0.96 | 0.97 | 0.83 |
| f_Erysipelotrichaceae | 0.0067 | 0.0086 | 0.0018 | 0.0013 | 0.0000 | 0.27 | 0.81 | 0.84 | 0.62 | 0.81 | 0.83 | 0.61 |
| f_[Mogibacteriaceae] | 0.0005 | 0.0017 | 0.0001 | 0.0044 | 0.0001 | 0.28 | 0.80 | 0.61 | 0.87 | 0.79 | 0.59 | 0.85 |
| f_Pseudomonadaceae | 0.1054 | 0.0386 | 0.0305 | 0.0411 | 0.0000 | 0.29 | 0.69 | 0.64 | 0.64 | 0.67 | 0.64 | 0.64 |
| f_Fusobacteriaceae | 0.0024 | 0.0043 | 0.0007 | 0.0029 | 0.0001 | 0.29 | 0.67 | 0.69 | 0.49 | 0.65 | 0.68 | 0.50 |
| f_Pseudonocardiaceae | 0.0006 | 0.0041 | 0.0002 | 0.0008 | 0.0020 | 0.31 | 0.79 | 0.83 | 0.59 | 0.79 | 0.83 | 0.57 |
| f_Leuconostocaceae | 0.0041 | 0.0107 | 0.0014 | 0.0036 | 0.0000 | 0.35 | 0.79 | 0.80 | 0.63 | 0.78 | 0.79 | 0.62 |
| f_Moraxellaceae | 0.0941 | 0.0058 | 0.0430 | 0.0060 | 0.0000 | 0.46 | 0.73 | 0.60 | 0.75 | 0.70 | 0.57 | 0.73 |
| f_Methylobacteriaceae | 0.0045 | 0.0007 | 0.0021 | 0.0056 | 0.0000 | 0.47 | 0.77 | 0.59 | 0.89 | 0.76 | 0.58 | 0.88 |
| f_[Paraprevotellaceae] | 0.0026 | 0.0006 | 0.0012 | 0.0029 | 0.0032 | 0.48 | 0.67 | 0.46 | 0.80 | 0.67 | 0.45 | 0.78 |
| f_Sphingomonadaceae | 0.0129 | 0.0138 | 0.0293 | 0.0119 | 0.0000 | 2.27 | 0.70 | 0.61 | 0.71 | 0.68 | 0.59 | 0.69 |
| f_Nocardioidaceae | 0.0004 | 0.0023 | 0.0011 | 0.0004 | 0.0144 | 2.39 | 0.69 | 0.81 | 0.44 | 0.69 | 0.79 | 0.42 |
| f_Lactobacillaceae | 0.0302 | 0.0779 | 0.0883 | 0.0085 | 0.0000 | 2.92 | 0.85 | 0.88 | 0.67 | 0.84 | 0.86 | 0.68 |
| f_Burkholderiaceae | 0.0017 | 0.0061 | 0.0078 | 0.0405 | 0.0000 | 4.55 | 0.96 | 0.82 | 0.92 | 0.95 | 0.81 | 0.91 |
| f_Aerococcaceae | 0.0026 | 0.0464 | 0.0202 | 0.0216 | 0.0000 | 7.79 | 0.72 | 0.71 | 0.61 | 0.72 | 0.71 | 0.61 |
| f_Nocardiopsaceae | 0.0000 | 0.0006 | 0.0001 | 0.0005 | 0.1213 | 8.02 | 0.65 | 0.70 | 0.51 | 0.64 | 0.69 | 0.47 |
| f_Rhodocyclaceae | 0.0003 | 0.0039 | 0.0038 | 0.0408 | 0.0000 | 13.55 | 0.90 | 0.72 | 0.90 | 0.89 | 0.71 | 0.90 |
| f_S24-7 | 0.0037 | 0.0735 | 0.0542 | 0.0369 | 0.0000 | 14.82 | 0.70 | 0.73 | 0.55 | 0.68 | 0.71 | 0.52 |
| f_Eubacteriaceae | 0.0000 | 0.0005 | 0.0002 | 0.0030 | 0.0015 | 15.51 | 0.78 | 0.59 | 0.89 | 0.77 | 0.58 | 0.88 |
| f_Desulfovibrionaceae | 0.0006 | 0.0332 | 0.0096 | 0.0679 | 0.0000 | 15.96 | 0.84 | 0.73 | 0.84 | 0.83 | 0.72 | 0.84 |
| f_Comamonadaceae | 0.0022 | 0.0853 | 0.1093 | 0.0161 | 0.0000 | 50.44 | 0.86 | 0.88 | 0.73 | 0.86 | 0.87 | 0.72 |
| f_Methylophilaceae | 0.0000 | 0.0427 | 0.0031 | 0.0104 | 0.0000 | 85.34 | 0.77 | 0.76 | 0.63 | 0.77 | 0.76 | 0.63 |
| f_Coxiellaceae | 0.0000 | 0.0054 | 0.0002 | 0.0001 | 0.0018 | 284.80 | 0.70 | 0.97 | 0.37 | 0.68 | 0.96 | 0.36 | genus *Salinicoccus*, the genus *Jeotgalicoccus*, the genus *Desulfovibrio*, the genus *Burkholderia*, the genus *Novosphingobium*, the genus *Comamonas*, the genus *Cloacibacterium*, the genus *Dechloromonas*, the genus *Thermomonas*, the genus *Diaphorobacter*, the genus *Pedomicrobium*, the genus KD1-23, the genus *Zoogloea*, the genus *Methylophaga*, and the genus *Haererehalobacter* as a biomarker exhibited significant diagnostic performance for ovarian cancer (see Table 10 and FIG. 10).

TABLE 10

|  | Control | | Ovarian Cancer | | | | | Training | | | Testing | | |
| --- | --- | --- | --- | --- | --- | --- | --- | --- | --- | --- | --- | --- | --- |
|  | Mean | SD | Mean | SD | p value | Ratio | AUC | sensitivity | specificity | AUC | sensitivity | specificity |
| g_Morganella | 0.0091 | 0.0243 | 0.0000 | 0.0002 | 0.0000 | 0.00 | 0.80 | 0.98 | 0.54 | 0.79 | 0.98 | 0.53 |
| g_Rhizobium | 0.0034 | 0.0036 | 0.0000 | 0.0001 | 0.0000 | 0.00 | 0.96 | 0.99 | 0.88 | 0.95 | 0.99 | 0.88 |
| g_Exiguobacterium | 0.0017 | 0.0077 | 0.0000 | 0.0001 | 0.0134 | 0.01 | 0.70 | 0.92 | 0.43 | 0.70 | 0.89 | 0.43 |
| g_Cupriavidus | 0.0333 | 0.0988 | 0.0016 | 0.0028 | 0.0002 | 0.05 | 0.73 | 0.78 | 0.58 | 0.73 | 0.77 | 0.56 |
| g_Ralstonia | 0.0165 | 0.0483 | 0.0012 | 0.0026 | 0.0003 | 0.07 | 0.70 | 0.75 | 0.54 | 0.69 | 0.73 | 0.53 |
| g_Cellulomonas | 0.0007 | 0.0017 | 0.0001 | 0.0003 | 0.0000 | 0.08 | 0.67 | 0.80 | 0.43 | 0.67 | 0.79 | 0.42 |
| g_Sporosarcina | 0.0010 | 0.0025 | 0.0001 | 0.0004 | 0.0000 | 0.08 | 0.71 | 0.80 | 0.53 | 0.71 | 0.77 | 0.51 |
| g_Proteus | 0.0112 | 0.0213 | 0.0010 | 0.0021 | 0.0000 | 0.09 | 0.82 | 0.87 | 0.60 | 0.82 | 0.88 | 0.60 |
| g_Leptotrichia | 0.0012 | 0.0026 | 0.0001 | 0.0006 | 0.0000 | 0.12 | 0.70 | 0.81 | 0.45 | 0.69 | 0.81 | 0.43 |
| g_SMB53 | 0.0041 | 0.0053 | 0.0005 | 0.0011 | 0.0000 | 0.12 | 0.86 | 0.85 | 0.69 | 0.85 | 0.83 | 0.67 |
| g_Prevotella | 0.0695 | 0.0779 | 0.0093 | 0.0085 | 0.0000 | 0.13 | 0.85 | 0.88 | 0.67 | 0.84 | 0.88 | 0.67 |
| g_Oribacterium | 0.0004 | 0.0013 | 0.0001 | 0.0004 | 0.0018 | 0.14 | 0.65 | 0.74 | 0.47 | 0.63 | 0.73 | 0.46 |
| g_Pediococcus | 0.0005 | 0.0012 | 0.0001 | 0.0005 | 0.0004 | 0.16 | 0.69 | 0.77 | 0.51 | 0.68 | 0.75 | 0.49 |
| g_Paraprevotella | 0.0008 | 0.0020 | 0.0001 | 0.0006 | 0.0003 | 0.16 | 0.72 | 0.75 | 0.57 | 0.71 | 0.74 | 0.54 |
| g_Methylobacterium | 0.0035 | 0.0050 | 0.0006 | 0.0015 | 0.0000 | 0.17 | 0.78 | 0.84 | 0.54 | 0.77 | 0.83 | 0.53 |
| g_Mucispirillum | 0.0003 | 0.0008 | 0.0001 | 0.0004 | 0.0004 | 0.17 | 0.68 | 0.75 | 0.50 | 0.67 | 0.74 | 0.51 |
| g_Catenibacterium | 0.0039 | 0.0099 | 0.0007 | 0.0017 | 0.0002 | 0.18 | 0.74 | 0.80 | 0.50 | 0.72 | 0.78 | 0.49 |
| g_Parabacteroides | 0.0075 | 0.0102 | 0.0016 | 0.0029 | 0.0000 | 0.21 | 0.83 | 0.82 | 0.68 | 0.82 | 0.82 | 0.67 |
| g_Collinsella | 0.0073 | 0.0100 | 0.0016 | 0.0029 | 0.0000 | 0.22 | 0.76 | 0.79 | 0.57 | 0.75 | 0.78 | 0.57 |
| g_Anaerostipes | 0.0007 | 0.0015 | 0.0002 | 0.0013 | 0.0024 | 0.26 | 0.70 | 0.78 | 0.51 | 0.69 | 0.76 | 0.48 |
| g_Pseudomonas | 0.0999 | 0.0829 | 0.0269 | 0.0143 | 0.0000 | 0.27 | 0.87 | 0.90 | 0.74 | 0.86 | 0.90 | 0.73 |
| g_Butyricimonas | 0.0011 | 0.0021 | 0.0003 | 0.0016 | 0.0011 | 0.30 | 0.71 | 0.74 | 0.55 | 0.69 | 0.72 | 0.53 |
| g_Fusobacterium | 0.0023 | 0.0046 | 0.0007 | 0.0020 | 0.0002 | 0.30 | 0.68 | 0.76 | 0.54 | 0.67 | 0.74 | 0.52 |
| g_Weissella | 0.0016 | 0.0027 | 0.0005 | 0.0013 | 0.0000 | 0.31 | 0.70 | 0.74 | 0.56 | 0.68 | 0.71 | 0.53 |
| g_[Eubacterium] | 0.0015 | 0.0020 | 0.0005 | 0.0011 | 0.0000 | 0.31 | 0.74 | 0.77 | 0.56 | 0.73 | 0.75 | 0.56 |
| g_Dialister | 0.0052 | 0.0105 | 0.0017 | 0.0030 | 0.0002 | 0.33 | 0.68 | 0.68 | 0.56 | 0.67 | 0.69 | 0.54 |
| g_Actinomyces | 0.0039 | 0.0048 | 0.0014 | 0.0024 | 0.0000 | 0.35 | 0.72 | 0.75 | 0.53 | 0.70 | 0.73 | 0.52 |
| g_Odoribacter | 0.0004 | 0.0009 | 0.0002 | 0.0006 | 0.0027 | 0.36 | 0.67 | 0.70 | 0.55 | 0.66 | 0.69 | 0.53 |
| g_Sphingomonas | 0.0102 | 0.0139 | 0.0039 | 0.0039 | 0.0000 | 0.38 | 0.74 | 0.75 | 0.58 | 0.72 | 0.74 | 0.58 |
| g_Bacteroides | 0.0434 | 0.0427 | 0.0176 | 0.0104 | 0.0000 | 0.40 | 0.78 | 0.77 | 0.64 | 0.76 | 0.75 | 0.62 |
| g_Turicibacter | 0.0025 | 0.0037 | 0.0011 | 0.0025 | 0.0004 | 0.45 | 0.65 | 0.68 | 0.51 | 0.65 | 0.68 | 0.50 |
| g_Enterococcus | 0.0087 | 0.0103 | 0.0041 | 0.0049 | 0.0000 | 0.47 | 0.67 | 0.72 | 0.50 | 0.64 | 0.71 | 0.48 |
| g_Dorea | 0.0020 | 0.0024 | 0.0010 | 0.0023 | 0.0004 | 0.50 | 0.71 | 0.71 | 0.63 | 0.70 | 0.70 | 0.62 |
| g_Lactobacillus | 0.0293 | 0.0331 | 0.0877 | 0.0679 | 0.0000 | 3.00 | 0.84 | 0.73 | 0.84 | 0.84 | 0.72 | 0.84 |
| g_Erwinia | 0.0005 | 0.0010 | 0.0016 | 0.0028 | 0.0000 | 3.40 | 0.66 | 0.51 | 0.70 | 0.65 | 0.50 | 0.69 |
| g_Staphylococcus | 0.0098 | 0.0127 | 0.0473 | 0.0526 | 0.0000 | 4.81 | 0.87 | 0.70 | 0.88 | 0.86 | 0.69 | 0.87 |
| g_Citrobacter | 0.0011 | 0.0042 | 0.0057 | 0.0183 | 0.0052 | 5.02 | 0.76 | 0.63 | 0.83 | 0.75 | 0.59 | 0.80 |
| g_Halomonas | 0.0004 | 0.0027 | 0.0021 | 0.0030 | 0.0000 | 5.08 | 0.78 | 0.59 | 0.85 | 0.78 | 0.58 | 0.83 |
| g_Sphingobium | 0.0011 | 0.0020 | 0.0059 | 0.0078 | 0.0000 | 5.40 | 0.73 | 0.55 | 0.81 | 0.72 | 0.54 | 0.80 |
| g_Gordonia | 0.0001 | 0.0005 | 0.0009 | 0.0022 | 0.0000 | 6.51 | 0.69 | 0.50 | 0.77 | 0.68 | 0.49 | 0.75 |
| g_Adlercreutzia | 0.0014 | 0.0023 | 0.0123 | 0.0108 | 0.0000 | 8.50 | 0.91 | 0.75 | 0.89 | 0.91 | 0.73 | 0.88 |
| g_Brevibacillus | 0.0001 | 0.0005 | 0.0014 | 0.0032 | 0.0000 | 16.91 | 0.67 | 0.46 | 0.79 | 0.67 | 0.46 | 0.79 |
| g_Aerocoecus | 0.0005 | 0.0016 | 0.0085 | 0.0155 | 0.0000 | 17.92 | 0.83 | 0.63 | 0.92 | 0.82 | 0.63 | 0.92 |
| g_Salinicoccus | 0.0001 | 0.0003 | 0.0011 | 0.0019 | 0.0000 | 18.47 | 0.73 | 0.48 | 0.88 | 0.71 | 0.47 | 0.84 |
| g_Jeotgalicoccus | 0.0007 | 0.0020 | 0.0147 | 0.0193 | 0.0000 | 20.50 | 0.91 | 0.76 | 0.92 | 0.90 | 0.75 | 0.92 |
| g_Desulfovibrio | 0.0003 | 0.0011 | 0.0096 | 0.0112 | 0.0000 | 30.29 | 0.92 | 0.77 | 0.94 | 0.92 | 0.77 | 0.93 |
| g_Burkholderia | 0.0002 | 0.0008 | 0.0068 | 0.0078 | 0.0000 | 33.52 | 0.87 | 0.71 | 0.96 | 0.86 | 0.71 | 0.95 |
| g_Novosphingobium | 0.0004 | 0.0013 | 0.0161 | 0.0206 | 0.0000 | 44.01 | 0.85 | 0.72 | 0.96 | 0.84 | 0.71 | 0.95 |
| g_Comamonas | 0.0002 | 0.0005 | 0.0104 | 0.0120 | 0.0000 | 59.71 | 0.89 | 0.77 | 0.96 | 0.89 | 0.76 | 0.95 |
| g_Cloacibacterium | 0.0003 | 0.0012 | 0.0273 | 0.0375 | 0.0000 | 81.10 | 0.93 | 0.81 | 0.96 | 0.93 | 0.80 | 0.95 |
| g_Dechloromonas | 0.0000 | 0.0000 | 0.0013 | 0.0026 | 0.0000 | 285.02 | 0.73 | 0.47 | 0.88 | 0.73 | 0.46 | 0.86 |
| g_Thermomonas | 0.0000 | 0.0000 | 0.0007 | 0.0014 | 0.0000 | 430.36 | 0.70 | 0.44 | 0.86 | 0.70 | 0.42 | 0.85 |
| g_Diaphorobacter | 0.0000 | 0.0000 | 0.0026 | 0.0036 | 0.0000 | 848.13 | 0.85 | 0.67 | 0.98 | 0.84 | 0.66 | 0.97 |
| g_Pedomicrobium | 0.0000 | 0.0000 | 0.0009 | 0.0023 | 0.0000 |  | 0.70 | 0.42 | 0.86 | 0.70 | 0.42 | 0.85 |
| g_KD1-23 | 0.0000 | 0.0000 | 0.0004 | 0.0008 | 0.0000 |  | 0.69 | 0.47 | 0.82 | 0.69 | 0.45 | 0.80 |
| g_Zoogloea | 0.0000 | 0.0000 | 0.0005 | 0.0011 | 0.0000 |  | 0.68 | 0.46 | 0.84 | 0.68 | 0.43 | 0.81 |
| g_Methylophaga | 0.0000 | 0.0000 | 0.0004 | 0.0012 | 0.0006 |  | 0.66 | 0.43 | 0.82 | 0.66 | 0.42 | 0.80 |
| g_Haererehalobacter | 0.0000 | 0.0000 | 0.0009 | 0.0027 | 0.0002 |  | 0.66 | 0.47 | 0.76 | 0.66 | 0.45 | 0.76 |

The above description of the present invention is provided only for illustrative purposes, and it will be understood by one of ordinary skill in the art to which the present invention pertains that the invention may be embodied in various modified forms without departing from the spirit or essential characteristics thereof. Thus, the embodiments described herein should be considered in an illustrative sense only and not for the purpose of limitation.

INDUSTRIAL APPLICABILITY

A method of providing information for ovarian cancer diagnosis through bacterial metagenomic analysis, according to the present invention, can be used to predict a risk for ovarian cancer and diagnose ovarian cancer by analyzing an increase or decrease in content of extracellular vesicles derived from specific bacteria through bacterial metagenomic analysis using a subject-derived sample. Extracellular vesicles secreted from bacteria existing in the environment are absorbed into the human body, and thus may directly affect the occurrence of cancer, and it is difficult to diagnose ovarian cancer early before symptoms thereof so that efficient treatment thereof is difficult. Thus, according to the present invention, a risk for ovarian cancer can be predicted through metagenomic analysis of bacteria-derived extracellular vesicles using a human body-derived sample, and thus the onset of ovarian cancer can be delayed or ovarian cancer can be predicted through appropriate management by early diagnosis and prediction of a risk group for ovarian cancer, and even after ovarian cancer occurs, early diagnosis for ovarian cancer can be implemented, thereby lowering the incidence of ovarian cancer and increasing therapeutic effects. In addition, the metagenomic analysis enables patients diagnosed with ovarian cancer to avoid exposure to causative factors predicted thereby, whereby the progression of cancer is ameliorated, or the recurrence of ovarian cancer can be prevented.

The invention claimed is:
1. A method for diagnosing an increased risk of ovarian cancer comprising:
 (a) obtaining a blood sample or a urine sample from a subject;
 (b) isolating bacteria-derived extracellular vesicles (EVs) from the blood sample or urine sample;
 (c) extracting DNA from the EVs;
 (d) performing a polymerase chain reaction (PCR) on the extracted DNA using a first primer consisting of SEQ ID NO:1 and a second primer consisting of SEQ ID NO:2 to produce PCR products;
 (e) sequencing PCR products;
 (f) analyzing the sequenced PCR products to determine the identity of the bacteria from which the EVs were derived and the quantity of the bacteria-derived EVs; and
 (g) diagnosing ovarian cancer by detecting an increase in the quantity of bacteria-derived EVs by two-fold or more in the blood sample from the subject as compared to that in blood samples obtained from normal, control individuals or an at least two-fold increase or decrease in the quantity of bacteria-derived EVs in the urine sample from the subject as compared to that in urine samples from normal, control individuals;
 wherein in (g),
 (i) the EVs are one or more EVs selected from the group consisting of: the genus *Burkholderia*-derived EVs, the genus *Adlercreutzia*-derived EVs, the genus *Jeotgalicoccus*-derived EVs, and the genus *Desulfovibrio*-derived EVs, that are isolated from a subject blood sample,
 the increase in the quantity of bacteria-derived EVs by two-fold or more is in the EVs selected from group consisting of the genus *Burkholderia*-derived EVs, the genus *Adlercreutzia*-derived EVs, the genus *Jeotgalicoccus*-derived EVs, and the genus *Desulfovibrio*-derived EVs,

SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)..(42)
<223> OTHER INFORMATION: n is a, c, g, or t

<400> SEQUENCE: 1
tcgtcggcag cgtcagatgt gtataagaga cagcctacgg gnggcwgcag            50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc       55 or
(ii) the EVs are one or more EVs selected from the group consisting of: the genus *Rhizobium*-derived EVs, the genus *Adlercreutzia*-derived EVs, the genus *Jeotgalicoccus*-derived EVs, the genus *Desulfovibrio*-derived EVs, and the genus *Diaphorobacter*-derived EVs that are isolated from a subject urine sample, the increase in the quantity of bacteria-derived EVs by two-fold or more is in the EVs selected from group consisting of the genus *Adlercreutzia*-derived extracellular vesicles, the genus *Jeotgalicoccus*-derived EVs, the genus *Desulfovibrio*-derived EVs, the genus *Cloacibacterium*-derived EVs, and the genus *Diaphorobacter*-derived EVs, and the decrease in the quantity of bacteria-derived EVs by two-fold or more is in the genus *Rhizobium*-derived EVs.

2. The method of claim 1, wherein the blood is whole blood, serum, plasma, or blood mononuclear cells.

* * * * *